United States Patent
Tillema et al.

(10) Patent No.: US 8,513,372 B2
(45) Date of Patent: Aug. 20, 2013

(54) ASYMMETRIC PHOTO-PATTERNABLE SOL-GEL PRECURSORS AND THEIR METHODS OF PREPARATION

(75) Inventors: Joshua Tillema, Oceanside, CA (US); Mohanalingam Kathaperumal, Oceanside, CA (US); Wan-Yun Hsieh, San Diego, CA (US); Michiharu Yamamoto, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 286 days.

(21) Appl. No.: 13/125,955

(22) PCT Filed: Sep. 23, 2009

(86) PCT No.: PCT/US2009/058098
§ 371 (c)(1),
(2), (4) Date: Apr. 25, 2011

(87) PCT Pub. No.: WO2010/053629
PCT Pub. Date: May 14, 2010

(65) Prior Publication Data
US 2011/0207049 A1 Aug. 25, 2011

Related U.S. Application Data

(60) Provisional application No. 61/111,454, filed on Nov. 5, 2008.

(51) Int. Cl.
*C08G 77/00* (2006.01)

(52) U.S. Cl.
USPC .......................................................... 528/43

(58) Field of Classification Search
USPC .......................................................... 528/43
See application file for complete search history.

(56) References Cited

U.S. PATENT DOCUMENTS

| 5,100,764 | A | 3/1992 | Paulson et al. |
| 5,991,493 | A | 11/1999 | Dawes et al. |
| 6,054,253 | A | 4/2000 | Fardad et al. |
| 6,391,515 | B1 | 5/2002 | Su et al. |
| 6,908,723 | B2 | 6/2005 | Fardad et al. |
| 2003/0013043 | A1 | 1/2003 | Inno et al. |
| 2006/0293478 | A1 | 12/2006 | Rantala et al. |
| 2008/0026322 | A1 | 1/2008 | Ogihara et al. |
| 2008/0076059 | A1 | 3/2008 | Abdallah et al. |

FOREIGN PATENT DOCUMENTS

| EP | 0 164 598 | 12/1985 |
| EP | 0277023 | 1/1987 |
| EP | 1317005 | 6/2003 |
| JP | 2004-10849 | 1/2004 |
| JP | 2005-290312 | 10/2005 |
| WO | WO 02/091083 | 11/2002 |
| WO | WO 2005/103062 | 11/2005 |
| WO | WO 2007/088640 | 8/2007 |

OTHER PUBLICATIONS

Chia-Chi Teng, "Precision measurements of the optical attenuation profile along the propagation path in thin-film waveguides." Applied Optics, vol. 32, No. 7, pp. 1051-1054 Mar. 1, 1993.
Corey et al., "Tricyclic Heterocycles with Bifunctional Silicon Centers," Journal of Organometallic Chemistry, 1986, vol. 304, pp. 93-105, p. 96, para 4 to p. 97, para 1; Table 2.
Dulcey et al., "Photochemistry and Patterning of Self-Assembled Monolayer Films Containing Aromatic Hydrocarbon Functional Groups," Langmuir, 1996, vol. 12, p. 1638-1650.
Leet et al, "Synthesis and Optical Properties of Sol-Gel Hybrid Materials that Contain Perflurocyclobutyl Groups," Macromolecular Rapid Communications, 2006, vol. 27 (16), p. 1330-1334.
Oshita et al., "Convenient synthesis of alkoxyhalosilanes from hydrosilanes," J. Organometallic Chem. 689 (2004) 3258.
International Search Report issued on Nov. 11, 2009 in PCT/US09/58098.

*Primary Examiner* — Kuo-Liang Peng
(74) *Attorney, Agent, or Firm* — Knobbe Martens Olson & Bear, LLP

(57) ABSTRACT

Described herein are photo-patternable sol-gel precursors and their methods of preparation. The sol-gel precursors are thermally stable and form compositions that have high refractive indices and low optical loss values. The precursors can be used to make sol-gel compositions that are ideally suited toward optical waveguide applications in the realm of telecommunications wavelengths.

27 Claims, 5 Drawing Sheets

ASYMMETRIC PHOTO-PATTERNABLE SOL-GEL PRECURSORS AND THEIR METHODS OF PREPARATION

CROSS-REFERENCE TO RELATED APPLICATIONS

This application claims priority to U.S. Provisional Application Ser. No. 61/111,454 filed on Nov. 5, 2008, entitled "ASYMMETRIC PHOTO-PATTERNABLE SOL-GEL PRECURSORS AND THEIR METHODS OF PREPARATION," the contents of which are hereby incorporated by reference in their entirety.

BACKGROUND OF THE INVENTION

1. Field of the Invention

The invention relates to high refractive index photo-patternable organic and organometallic sol-gel precursors and the methods by which they are prepared. The invention further relates to sol-gel compositions and polymers derived from sol-gel precursors. The materials described herein are useful in various optical waveguide applications.

2. Description of the Related Art

Advances in fiber-optics and integrated optics have been made to address the rapidly growing need for high-bandwidth transmission of information, particularly for telecommunications. Needs, however, are still growing, placing additional demands on increasing rates of transmission as well as processing, switching, and routing of optical signals.

Particularly, future demands on transmission and processing will likely require bandwidth needs of greater than 100 GHz. The current transmission infrastructure relies upon modulators that are based on lithium niobate, and bandwidth is currently limited to 10 GHz. Additionally, lithium niobate is difficult to grow because it is a crystal and is also difficult to integrate into an optical circuit. See Dalton, L., "Nonlinear Optical Polymeric Materials: From Chromophore Design to Commercial Applications," *Advances in Polymer Science*, Vol. 158, pp. 1-86 (2001). Modulators based on organic and/or organometallic materials might overcome these deficiencies.

Desirable features of optical modulators include low insertion loss, high signal modulation efficiency, and durability under the conditions imposed by processing and operation. An example of a device structure upon which organic modulators are built is the Mach-Zehnder modulator. This modulator is a multi-layer device comprised of substrates, electrodes, cladding, and waveguide layers.

Recently, particular attention has been given to the materials required for cladding and waveguide layers. Desirably, these materials would have (1) low optical transmission losses (<1 dB/cm) in the realm of telecommunications wavelengths (1300-1600 nm), (2) high-conductivity to increased poling efficiency, (3) compatibility with various substrates, such as glass and quartz, (4) refractive indexes greater than 1.40, (5) good chemical and thermal stability, and (6) UV-visible light patternability. Sol-gel chemistry using organo-silicones has been investigated. See Hench, et al., "The Sol-Gel Process," *Chem. Rev.* 1990, 90, 33-72.

U.S. Pat. No. 6,391,515 to Su et al., the contents of which are hereby incorporated by reference, describes a process by which sol-gel optical waveguides are manufactured. U.S. Pat. No. 6,054,253 to Fardad et al., the contents of which are hereby incorporated by reference, discloses a photo-lithographic process by which ridge waveguides are made. However, neither of these references contains a disclosure as to the manufacture of low optical loss, high refractive index waveguides for the telecommunication wavelength range of 1300-1600 nm. U.S. Pat. No. 6,908,723 to Fardad et al., the contents of which are hereby incorporated by reference, discloses photo-patternable sol-gels having a refractive index of about 1.50 at 1550 nm by introducing C—F bonds along with a metal refractive index adjuster, preferably titanium, to a sol-gel. However, the maximum refractive index disclosed by Fardad et al. was only about 1.50. Furthermore, the reference describes methods that use metal oxides other than silicon oxide to obtain patterned sol-gel materials, such as Ti—O bonds and Zr—O bonds.

JP 2005-290312 to Matsumoto et al. lists a phenyl derivative of a bis-substituted dialkoxysilane. However, the compositions described by Matsumoto et al. are unrelated to optical waveguides. Furthermore, Matsumoto et al. fail to describe a synthesis for the bis-substituted dialkoxysilane. Oshita et al., "Convenient synthesis of alkoxyhalosilanes from hydrosilanes," *J. Organometallic Chem.* 689 (2004) 3258, reports the preparation of phenyldialkoxysilanes using $PdCl_2$. However, the catalyst described by Oshita et al. only works with aromatics having certain substitution patterns, and will not effect transformation on arylsilanes with ortho substitution. Corey, et al., *Organometallic Chem.* 304 (1986) 93-105, discloses rhodium catalyzed dehydrogenative coupling of alcohols to silanes via chloro(tris-triphenylphosphine)rhodium(I). However, Corey et al. do not disclose a controlled addition using methanol and ethanol with the resulting products containing a Si—H bond. The only chemistry done under a controlled addition was with tert-butyl alcohol, which results in a more stabile structure that can survive harsher conditions, due to the enhanced steric inhibition of the larger tert-butyl group to chemistry involving the silicon center. This enhanced steric inhibition significantly reduces the reactivity of the Si—H in further transformations, possibly affecting the choice of catalysts that could be used.

European Patent Appl. Pub. No. 0277023 to Kouji, et al. describes the hydrosilylation of allyl methacrylate to a tri-alkoxysilane using $H_2PtCl_6$. WO 2005/103062 to Eilenstine et al. discloses a method of hydrosilylating trialkoxysilanes to terminal olefins using a rhodium catalyst, but at an elevated temperature unsuitable for the functional groups present. However, there remains a need for improved sol-gel compositions having low optical loss coupled with high refractive index values and methods of making thereof.

SUMMARY OF THE INVENTION

Sol-Gel chemistry is particularly attractive for modulator applications in that it involves relatively simple chemistry that can be flexible depending on particular needs. Sol-gels are produced at room temperature by stirring alkoxysilanes in an organic solvent with a catalytic amount of acid. The resulting silanols can be spin-casted and cured at medium temperature under vacuum to yield high-quality optical films. Compositions can be prepared with the aforementioned method to tailor the material to particular needs. Sol-gels can be made photo-patternable with the introduction of siloxy compounds organically modified to include light-sensitive cross-linkable functional groups, such as methacrylate, acrylate, allyl, or epoxy groups.

A mixture comprising a multifunctional monomer that can be used to prepare a waveguide material is highly desirable because it can provide a reduction in the number of necessary manufacturing steps. For example, a composition that polymerizes from a multifunctional monomeric ingredient can be made in a single container without the need for multiple processing steps. Such a monomeric ingredient could provide multiple functionalities. For example, the monomer could contain a photo-patternable group (e.g. cross-linkable group) along with a group that increases the refractive index of the material. Additionally, the monomer could also possess groups that enable sol-gel polymerization for ease of manufacture.

The synthesis of such a monomer is difficult because of the obstacles that are present in synthesizing a molecule having the combination of functional groups desired to from a material useful as a waveguide. Synthesizing a material having each of these types of groups represents a difficult and unique synthetic challenge. For example, a trialkoxysilyl group that would enable sol-gel polymerization is difficult to place on a photo-patternable group because the basic conditions necessary to effect this synthesis may cause anionic polymerization of the photo-patternable group.

Alternatively, incorporating a photo-patternable group on a trialkoxysilyl-containing aromatic compound is also difficult, because there is a need for functional groups, such as alcohols, for coupling to occur. However, if these types of functional groups are indeed present, then they tend to inhibit the addition of the trialkoxysilyl group in the first place. Therefore, in an embodiment disclosed herein is a method of preparing a multifunctional monomer that contains both a photo-patternable group and an aromatic functional group by asymmetric bis-substitution of a dialkoxysilane. The alkoxysilane groups on the molecule allow it to be subject to sol-gel polymerization.

An embodiment provides a sol-gel precursor comprising a monomer according to the formula (I):

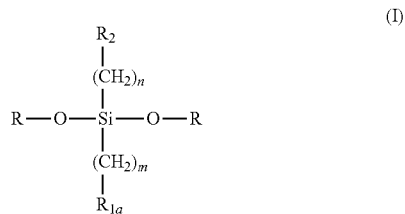

(I)

wherein $R_{1a}$ is an optionally substituted aromatic group, the aromatic group being selected from the group consisting of biphenyl, naphthyl, anthracenyl, phenanthrenyl, quinolinyl, tetracenyl, pentacenyl, pyrenyl, and perylenyl, $R_2$ is a photo-cross-linkable group comprising at least one of a methacrylate group, an acrylate group, an alkenyl group, a vinyl group, an epoxy group, or an acryloxy group, each R is independently selected to be a lower alkyl group or a lower alkoxyalkyl group, m is selected to be an integer in the range of 0 to about 10, and n is selected to be an integer in the range of 2 to about 10. The monomer can be used to form sol-gel compositions, which can further be processed to form a polymer material. Also described herein are methods of manufacturing the sol-gel precursor monomers and optical devices.

Embodiments of the multifunctional monomers described herein can participate in sol-gel chemistry due to the presence of an alkoxysilane functional group. This alkoxysilane functional group hydrolyzes upon exposure to an aqueous acid and produces a silanol (e.g., the sol). The sol can then be spin-casted and dried to a gel. The formed gel can then be processed to an aerogel or xerogel, depending on the conditions selected by one having ordinary skill in the art. Such processes are well-known and/or may be determined by routine experimentation guided by the present disclosure. Once dried, the sol forms excellent films that are insoluble in various common processing solvents used in the manufacture of other layers in a modulator/multi-layer device.

DETAILED DESCRIPTION OF THE PREFERRED EMBODIMENT

Figure 1:
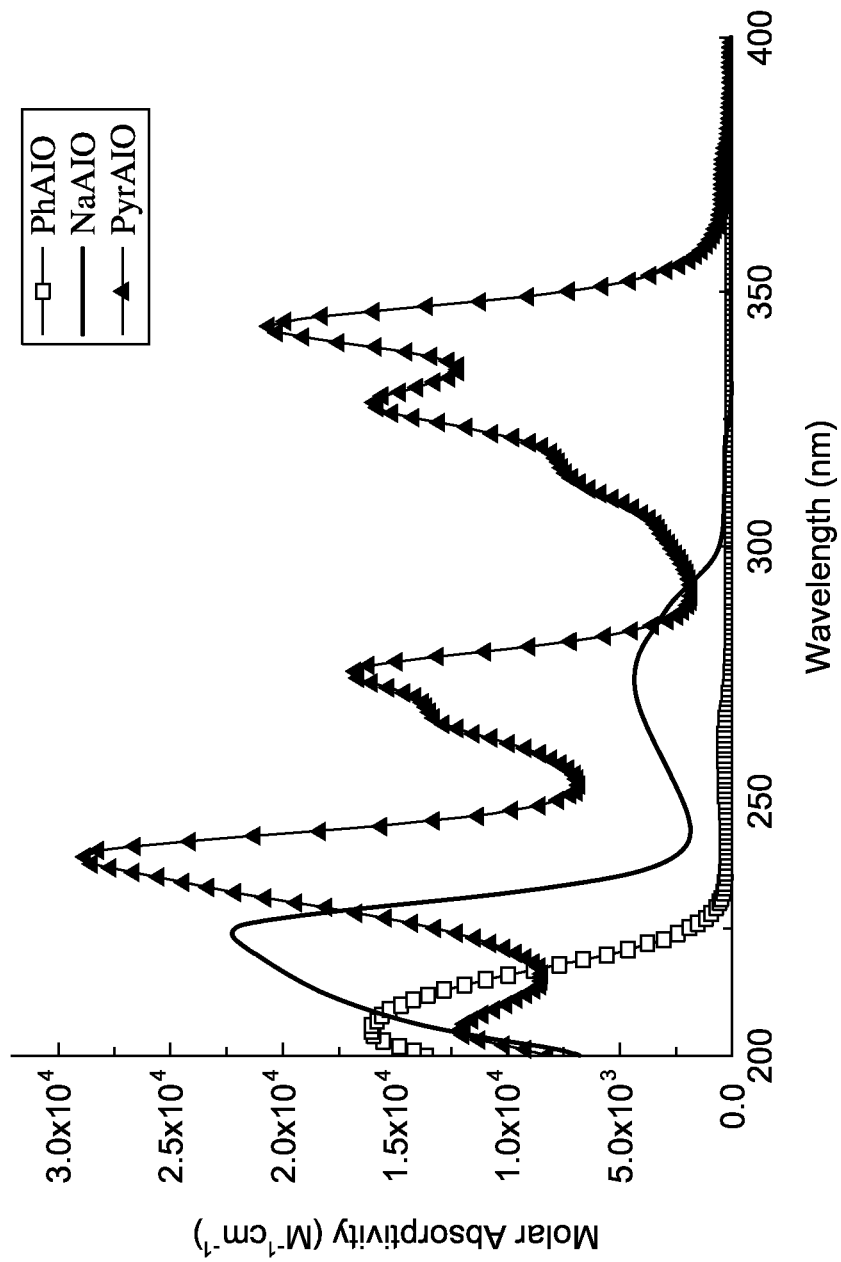
FIG. 1 is a plot showing superimposed absorption spectra for PhAIO, NaAIO, and PyrAIO.

An embodiment provides a sol-gel precursor comprising a monomer according to the formula (I), as described above. In an embodiment, $R_{1a}$ is an aromatic group. The aromatic group in $R_{1a}$ can be selected from the group consisting of biphenyl, naphthyl, anthracenyl, phenanthrenyl, quinolinyl, tetracenyl, pentacenyl, pyrenyl, and perylenyl.

In an embodiment, the aromatic group can be "optionally substituted" with one or more substituent groups. For example, the aromatic group can be completely non-substituted, partially substituted, or completely substituted by substituent groups. When substituted, each of the substituent group(s) is(are) are independently selected from a halogen atom or a deuterium atom. Non-limiting examples of possible substituent group(s) include fluorine, chlorine, bromine, iodine, and deuterium. In an embodiment, the aromatic group can be perfluorinated or perchlorinated. The amount of substitution on each of the aromatic groups in the sol-gel composition can be independently selected. For example, a phenyl ring can be substituted with one, two, three, four, or five substituent groups and a naphthyl ring can be substituted with one, two, three, four, five, six, or seven substituent groups.

In an embodiment, $R_2$ is a photo-cross-linkable group. The photo cross-linkable group can comprise various groups that cross-link upon irradiation with light. Preferably, the photo cross-linkable group comprises a double bond. In an embodiment, the photo-cross-linkable group comprises a methacrylate group, an acrylate group, an alkenyl group, a vinyl group, an epoxy group, or an acryloxy group. The monomer can be polymerized, and then the cross-linkable group can be cross-linked. In an embodiment, upon irradiation with light, for example, UV light, the photo cross-linkable group reacts to form covalent bonds that link various molecular chains within the polymer to one another. UV radiation can be performed, for example, after appropriate masking and patterning steps.

When the sol-gel or polymer is cross-linked, the degree of cross-linking can vary and be adjusted by those having ordinary skill in the art. Factors used to control the degree of cross-linking include the number of cross-linkable units dispersed throughout the sol-gel composition and the polymer, the distance between cross-linkable units, the amount of time the sol-gel composition or the polymer is exposed to irradiation, and the intensity of the irradiation. In an embodiment, the photo-cross-linkable group comprises at least one of a methacrylate group, an acrylate group, an alkenyl group, and an epoxy group.

Each R in formula (I) is independently selected to be a lower alkyl group or a lower alkoxyalkyl group. A "lower alkyl group" as described herein, means a branched or unbranched $C_1$-$C_5$ alkyl group. Suitable lower alkyl groups include methyl, ethyl, n-propyl, isopropyl, n-butyl, isobutyl, sec-butyl, t-butyl, and pentyl (and all isomers thereof). In an embodiment, each of the R groups in formula (I) is independently methyl or ethyl. A "lower alkoxyalkyl group" as defined herein, means a branched or unbranched $C_1$-$C_5$ alkoxy group that is followed by a $C_1$-$C_5$ alkyl group. Some examples of lower alkoxyalkyl groups include methoxymethyl, ethoxymethyl, methoxyethyl, and ethoxyethyl. In an embodiment, each R is independently selected from the group consisting of methyl, ethyl, propyl, and methoxymethyl.

The m in formula (I) is selected to be an integer in the range of 0 to about 10. In an embodiment, m is an integer in the range of 0 to about 4. In an embodiment, m is an integer in the range of 0 to about 2. In an embodiment, m is 0. In an embodiment, n in formula (I) is selected to be an integer in the range of 2 to about 10. In an embodiment, n in formula (I) is selected to be an integer in the range of about 3 to about 7. In an embodiment, n in formula (I) is selected to be an integer in the range of 3 to about 5. The value of m affects the molecular distance between the Si atom and the optionally substituted aromatic group, whereas the value of n affects the molecular distance between the Si atom and the photo-cross-linkable group.

Preferably, n and $R_2$ in formula (I) are selected to provide a photo-crosslinkable group with suitable spacing from the Si atom. In an embodiment, n and $R_2$ in formula (I) are selected such that the —$(CH_2)_n$—$R_2$ portion of formula (I) is a propylmethacrylate group, a propylacrylate group, an allyl group, or an epoxypropyl group. In an embodiment, the sol-gel precursor of formula (I) is selected from the group consisting of γ-(methacryloxy)propyl(2-naphthyl)diethoxysilane and γ-(methacryloxy)propyl(1-pyrenyl)diethoxysilane.

Another embodiment provides a method of making a sol-gel silane precursor monomer comprising an aromatic group and a photo-patternable group. An embodiment provides a method of making a sol-gel precursor of the formula (II):

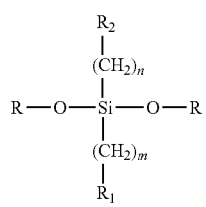

wherein $R_1$ is an optionally substituted aromatic group, the aromatic group being selected from the group consisting of phenyl, biphenyl, naphthyl, anthracenyl, phenanthrenyl, quinolinyl, tetracenyl, pentacenyl, pyrenyl, and perylenyl, $R_2$ is a photo-cross-linkable group comprising at least one of a methacrylate group, an acrylate group, an alkenyl group, a vinyl group, an epoxy group, or an acryloxy group, each R is independently selected to be a lower alkyl group or a lower alkoxyalkyl group, m is selected to be an integer in the range of 0 to about 10, and n is selected to be an integer in the range of 2 to about 10.

In an embodiment, the method comprises the steps of providing a solution that comprises a compound having a structure according to the formula (III):

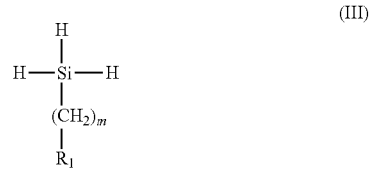

wherein $R_1$ and m are as defined above in formula (II), intermixing a transition metal catalyst with the solution, intermixing a compound having the formula R—OH with the solution, wherein R is as defined above in formula (II), and intermixing a compound having the formula $R_2$—$(CH_2)_{n-2}$—$CH$=$CH_2$ with said solution, wherein $R_2$ and n are as defined above in formula (II). The intermixing of the various ingredients can be conducted in any order. Each of the various ingredients, e.g. the compound having the formula R—OH, the compound having a structure according to the formula (III), and the compound having the formula $R_2$—$(CH_2)_{n-2}$—$CH$=$CH_2$, can be intermixed with the solution before, after, or simultaneously with each of the other ingredients.

The transition metal catalyst used in the formation of the silane precursor monomers can comprise a single transition metal catalyst. Preferably, the catalyst is capable of providing two distinct functions in the reaction. One function that the single transition metal catalyst provides is catalyzing the dehydrogenative coupling of the compound having the formula R—OH to an organosilane. Another function that a single transition metal catalyst provides is catalyzing the coupling of the terminal olefin in the compound having the formula $R_2$—$(CH_2)_{n-2}$—$CH$=$CH_2$ to an organodialkoxysilane. In an embodiment, the single transition metal catalyst comprises a Rhodium-based catalyst. For example, the single transition metal catalyst can comprise a Rhodium(I)-based catalyst. Such a catalyst comprises Rh(I). In an embodiment, the single transition metal catalyst comprises (acetylacetonato)dicarbonylrhodium(I).

The multifunctional precursor monomer compounds described herein can used in sol-gel processing and can be polymerized and fabricated into optical devices. In an embodiment, the sol-gel compositions can be formed into film layers that are useful in optical devices as waveguides. For example, in an embodiment, the sol-gel compositions can be spin-coated onto a substrate and dried in order to form a polymer. An embodiment provides a polymer comprising a recurring unit of the formula (IV):

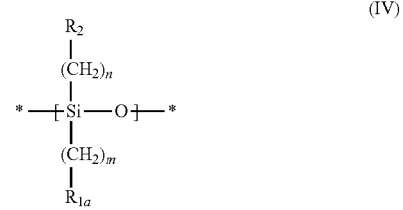

wherein $R_{1a}$ is an optionally substituted aromatic group. The aromatic group $R_{1a}$ in formula (IV) can be selected from the group consisting of biphenyl, naphthyl, anthracenyl, phenanthrenyl, quinolinyl, tetracenyl, pentacenyl, pyrenyl, and perylenyl. Each $R_2$, m, and n in formula (IV) is as defined in formula (I) above.

Embodiments of the polymers formed from the sol-gel compositions described herein have a high refractive index and low optical loss. Preferably, the sol-gel precursor is photo-patternable for use in waveguides and integrated optics with a refractive index greater than 1.50 and low optical loss in the 1300 to 1600 nm range used in telecommunications applications.

In an embodiment, the polymer or sol-gel has a refractive index greater than about 1.50 when measured at 1550 nm. In an embodiment, the polymer has a refractive index greater than about 1.55 when measured at 1550 nm. In an embodiment, the polymer has a refractive index greater than about 1.60 when measured at 1550 nm. In an embodiment, the polymer has a refractive index greater than about 1.61 when measured at 1550 nm. In an embodiment, the polymer has a refractive index greater than about 1.62 when measured at 1550 nm. In an embodiment, the polymer has a refractive index greater than about 1.63 when measured at 1550 nm. In an embodiment, the polymer has a refractive index greater than about 1.64 when measured at 1550 nm. In an embodiment, the polymer has a refractive index greater than about 1.65 when measured at 1550 nm. In an embodiment, the polymer has a refractive index greater than 1.657 when measured at 1550 nm.

The refractive index can also be measured at lower wavelengths. In an embodiment, the polymer or sol-gel has a refractive index greater than about 1.50 when measured at 633 nm. In an embodiment, the polymer has a refractive index greater than about 1.55 when measured at 633 nm. In an embodiment, the polymer has a refractive index greater than about 1.60 when measured at 633 nm. In an embodiment, the polymer has a refractive index greater than about 1.62 when measured at 633 nm. In an embodiment, the polymer has a refractive index greater than about 1.64 when measured at 633 nm. In an embodiment, the polymer has a refractive index greater than about 1.66 when measured at 633 nm. In an embodiment, the polymer has a refractive index greater than about 1.67 when measured at 633 nm. In an embodiment, the polymer has a refractive index greater than about 1.68 when measured at 633 nm. In an embodiment, the polymer has a refractive index greater than 1.69 when measured at 633 nm.

The polymers described herein achieve high refractive index due, in part, to the nature of the molecular composition. For example, the refractive indices of diamond, benzene, and hexane are 2.41, 1.501, and 1.375, respectively. Such data infers that the refractive index will proportionately decline with increased C—H bonding, and that a sample with a large number of hydrogen atoms relative to carbon atom would have a relatively low refractive index. Additionally, silicon dioxide has a refractive index of 1.45. Since the refractive index is desirably higher than 1.45 for optimal performance in the telecommunication wavelength, it is preferred to provide a composition having a relatively lower weight fraction of silicon dioxide. The sol-gel compositions and polymers described herein tend to have fewer C—H bonds and further a smaller number of Si—O bonds in order to provide materials with a refractive index greater than about 1.50.

Incorporation of methacryloxypropyl trimethoxysilane into sol-gel compositions allows them to be photo-patternable, but its addition has the consequence of increasing absorption losses, due to the increased presence of C—H and C—O bonds. Additionally, the trimethoxysilane further contains additional Si—O bonds. The sol-gel compositions and polymers described herein may be used in preferred embodiments to achieve a high refractive index (1) by minimization of C—H bonds by increasing aromatic systems, and (2) by minimization of Si—O bonds through decreasing or elimination of the methacryloxypropyl trimethoxysilane. Use of methacryloxypropyl trimethoxysilane in the sol-gel compositions and polymer compositions is optional. In an embodiment, the sol-gel composition is prepared without using methacryloxypropyl trimethoxysilane. The elimination of methacryloxypropyl trimethoxysilane also carries the additional benefit of reducing the number of manufacturing steps, since fewer components are needed to make the sol-gel material.

The materials described herein may be made photo-patternable by inclusion of a photo-crosslinkable group into the monomers, which are then polymerized. One example of a photo-crosslinkable group is a methacrylate functional group. The methacrylate group is photo-patternable because it is photo-polymerizable upon exposure to light, e.g., UV light. By attaching a photo-patternable functional group directly to the silicon atom (or through an (optionally hetero) alkylene linker), which also has an aromatic group attached thereto (directly or through an (optionally hetero) alkylene linker), the addition of methacryloxypropyl trimethoxysilane to the sol-gel composition becomes optional for photo-patterning.

The sol-gel compositions and polymer compositions described herein may be obtained from a sol-gel precursor. The sol-gel precursor can participate in sol-gel chemistry because of the presence of an alkoxysilane functional group. The alkoxysilane group hydrolyzes upon exposure to an aqueous acid, such as aqueous HCl, to produce a silanol (the sol). The sol can then be spin-casted and dried to a gel.

The sol-gel compositions and polymers can further be cross-linked. In an embodiment, the $R_2$ in formula (IV) is a group formed by photo-crosslinking said photo-cross-linkable group. Photo-crosslinking can be performed by exposing the material to UV light.

The gel can be processed into a polymeric material, such as an aerogel or a xerogel, by appropriate selection of processing conditions. Those skilled in the art, guided by the disclosure herein, will understand that the material may form excellent films, that once dried, may be insoluble in various common processing solvents used in the manufacture of other layers in a modulator or multi-layer device.

Embodiments of the polymers described herein possess excellent optical properties for use in various devices, including waveguides. FIG. 1 is a plot showing the molar absorptivity of various polymers as a function of wavelength in the range of about 200 nm to about 400 nm. The spectra of polymers comprised of γ-(methacryloxy)propyl(phenyl)diethoxysilane (PhAIO), γ-(methacryloxy)propyl(2-naphthyl)diethoxysilane (NaAIO), and γ-(methacryloxy)propyl(1-pyrenyl)diethoxysilane (PyrAIO) were measured. As shown in FIG. 1, a shift toward higher wavelength absorption was exhibited with increased size of the aromatic group attached to the polymer. A person having ordinary skill in the art can adjust the wavelength of light in which absorption occurs by selection of a larger aromatic group for incorporation into the polymer.

Figure 2:
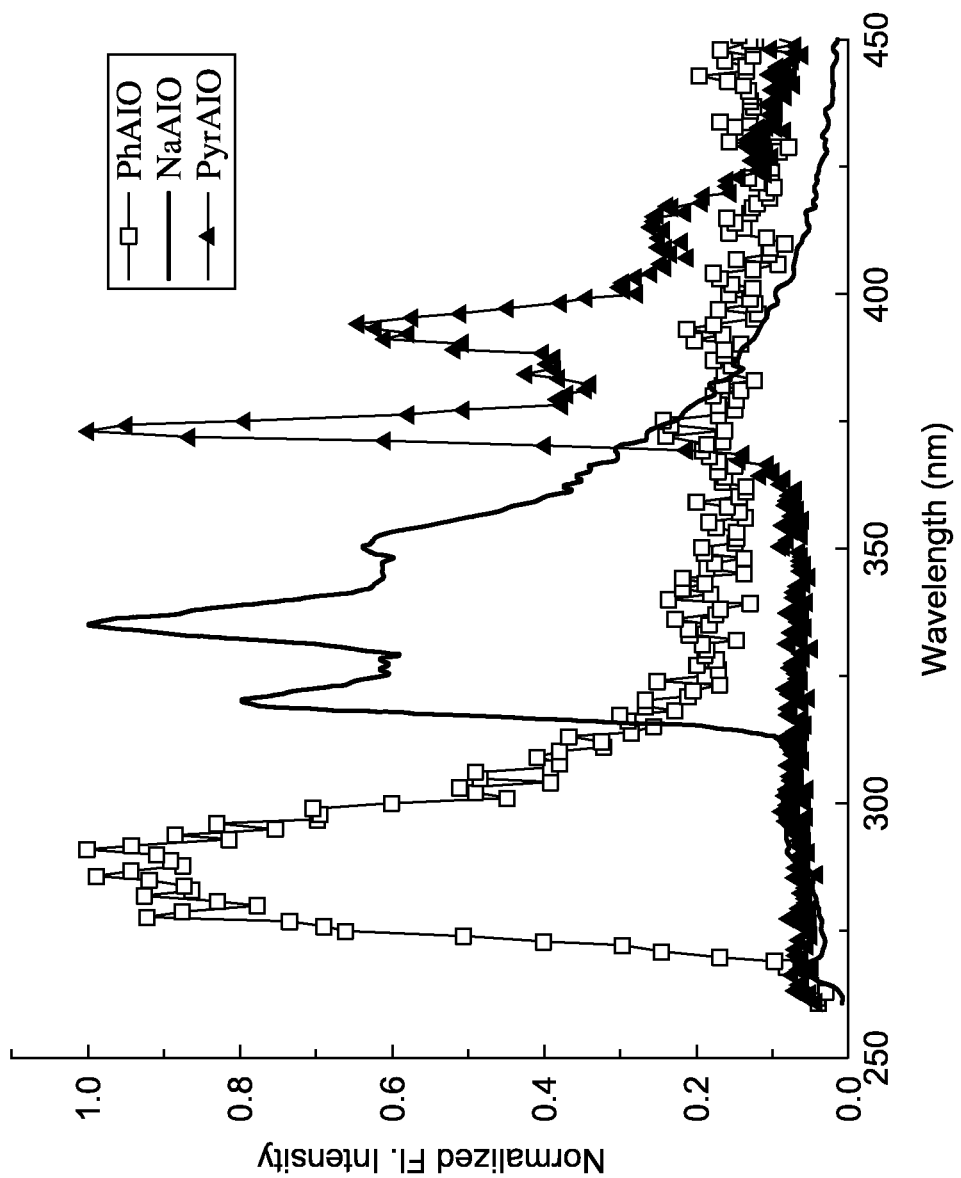
FIG. 2 is a plot showing superimposed normalized fluorescence spectra for PhAIO, NaAIO, and PyrAIO.

FIG. 2 is a plot showing the normalized fluorescence spectra for the same materials measured in FIG. 1. The emission of light from polymers also shows a shift towards higher wavelengths with increased size of the aromatic group attached to the polymer. With the ability to shift the wavelength of light emission of the polymer, a broad variety of device applications can be made.

Figure 3:
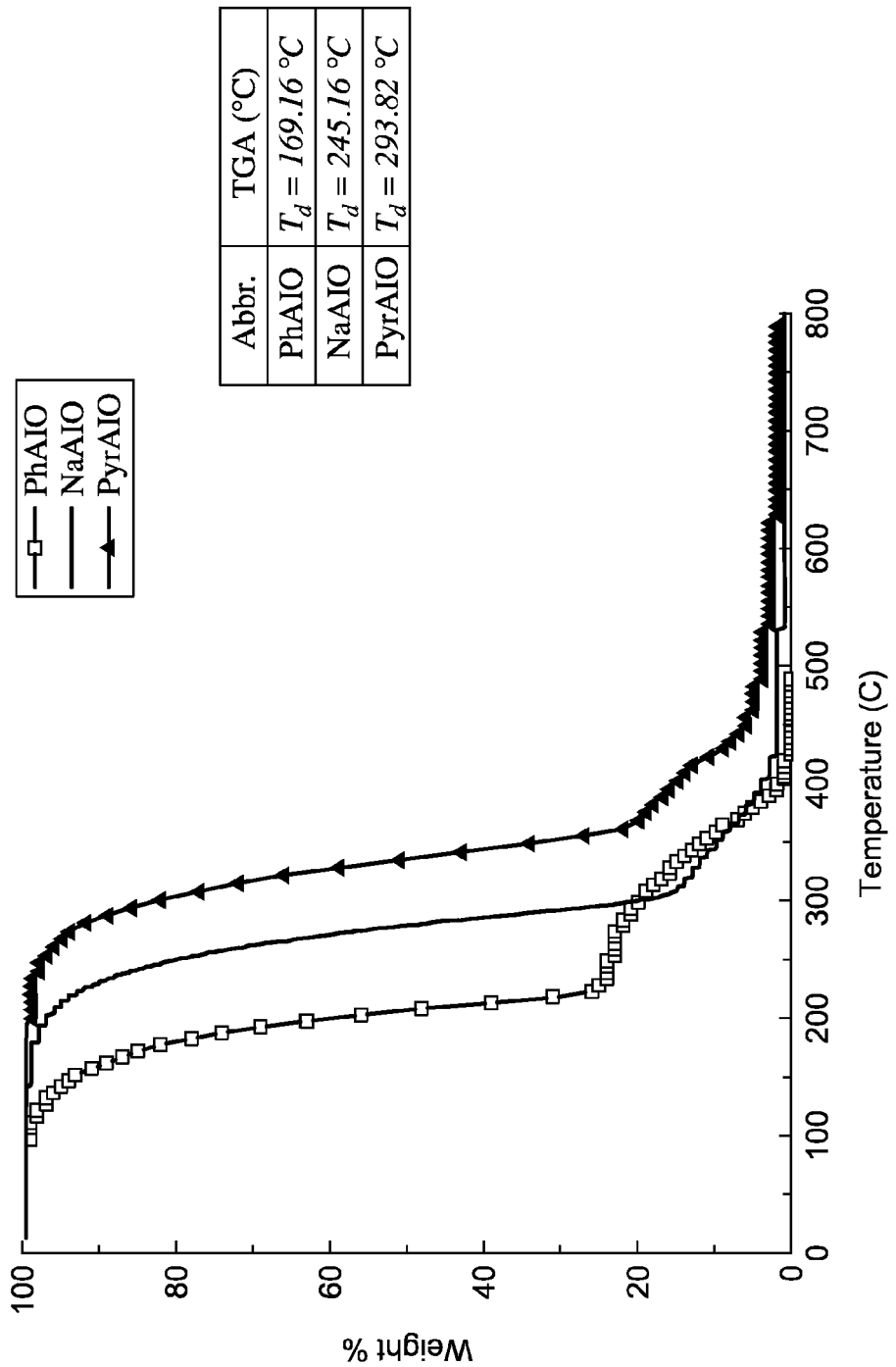
FIG. 3 is a plot showing superimposed TGA traces measuring thermal decomposition of neat liquids of PhAIO, NaAIO, and PyrAIO as a function of temperature.

The stability of each of the PhAIO, NaAIO, and PyrAIO monomers in a neat liquid was measured as a function of weight loss versus increased temperature. FIG. 3 is a plot of thermo gravimetric analyses (TGA) showing that the rate of decomposition decreased as the size of the aromatic ring increased. For example, the decomposition temperature of PhAIO monomer in neat liquid before sol-gel reaction was about 169° C. The decomposition temperature of NaAIO monomer in neat liquid before sol-gel reaction was about 245° C. And finally, the decomposition temperature of PyrAIO monomer in neat liquid before sol-gel reaction was about 294° C.

Figure 4:
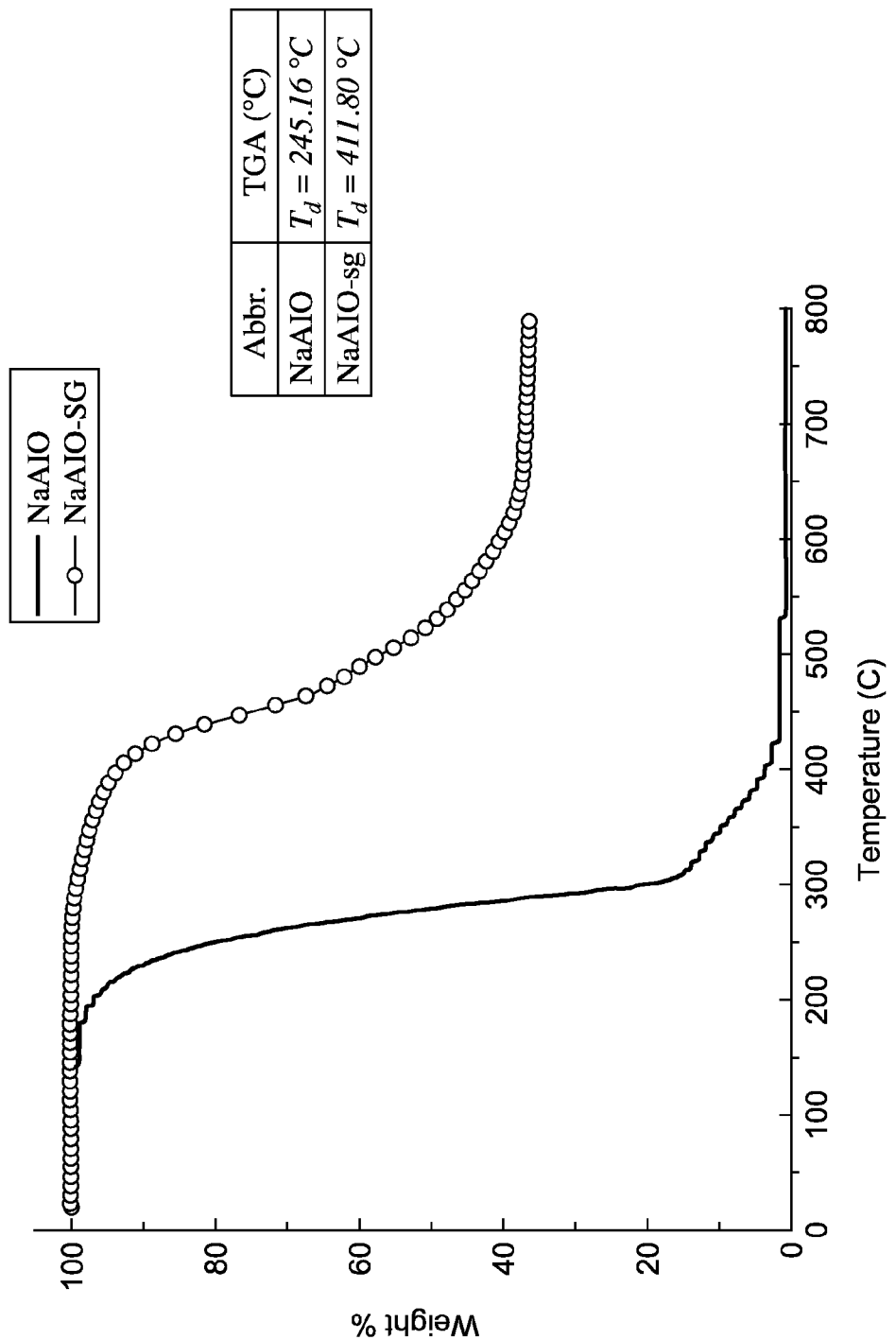
FIG. 4 is a plot comparing the TGA traces of NaAIO before and after the sol-gel reaction.
Figure 5:
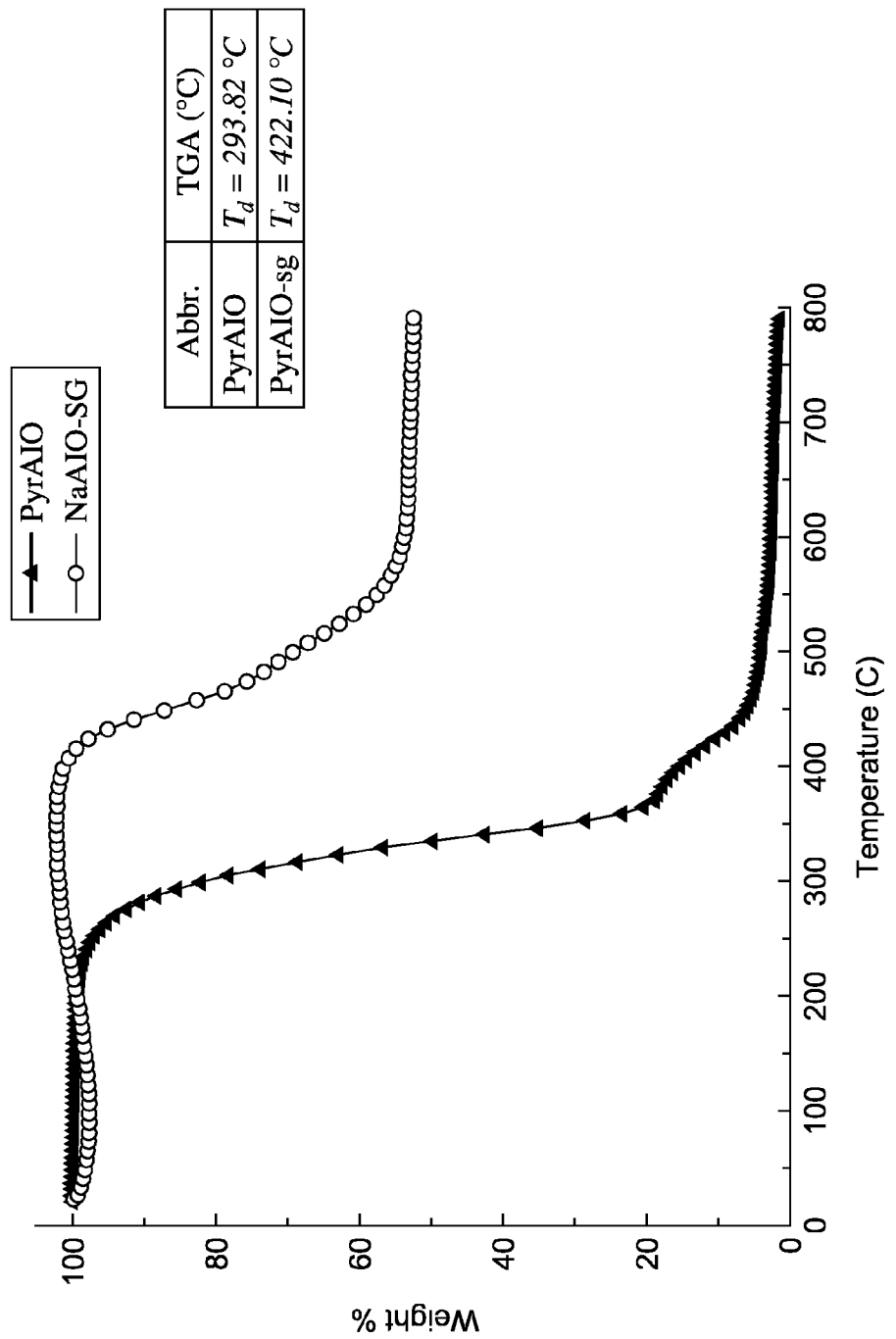
FIG. 5 is a plot comparing the TGA traces of PyrAIO before and after the sol-gel reaction.

The stability of the molecules increases after the monomer undergoes sol-gel reaction to form a polymer material. Each of the NaAIO and PyrAIO were polymerized in sol-gel to measure their stability against the associated monomer. FIG. 4 is a plot showing that the polymer (NaAIO-SG) does not begin to decompose until the temperature reaches about 412° C. Furthermore, the rate of weight loss begins to stabilize as the temperature further increases. For example, the rate of weight loss of the NaAIO-SG polymer begins to significantly decrease at about 600° C. The weight stabilizes at temperatures of about 800° C. or greater. FIG. 5 is a plot showing a similar result with the polymer PyrAIO-SG, which also exhibits stability at similarly high temperatures. The ability of the polymers to remain stable at higher temperatures renders them particularly useful in optical device and waveguide applications.

In an embodiment, the polymers described herein are thermally stable at about 600° C. or higher. In an embodiment, the polymers described herein are thermally stable at about 650° C. or higher. In an embodiment, the polymers described herein are thermally stable at about 700° C. or higher. In an embodiment, the polymers described herein are thermally stable at about 750° C. or higher. In an embodiment, the polymers described herein are thermally stable at about 800° C. or higher.

Also described herein are sol-gel compositions. In an embodiment, the sol-gel composition comprises a compound according to the formula (V):

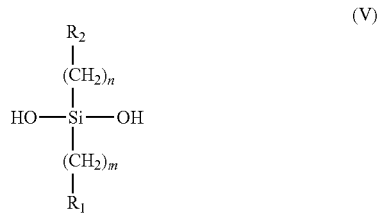

(V)

wherein $R_1$ is an optionally substituted aromatic group as described above with respect to formula (II) and $R_2$ is a photo-cross-linkable group as described above with respect to formulae (I) and (II). Each m and n in formula (V) is as defined in formulae (I) and (II) above.

In an embodiment, the sol-gel composition comprises a solvent. In an embodiment, the solvent is present in an amount of at least about 10% by weight based on the weight of the composition. In an embodiment, the solvent is present in an amount of at least 20% by weight. In an embodiment, the solvent is present in an amount of at least 30% by weight. In an embodiment, the solvent is present in an amount of at least 405% by weight. In an embodiment, the solvent is present in an amount of at least 50% by weight. Various solvents can be used. In an embodiment, the solvent comprises tetrahydrofuran.

The sol-gel compositions described herein can be prepared according to a variety of methods. For example, the sol-gel compositions can be prepared using a single type of organically modified bi-substituted silane precursor. Additionally, other organically modified silane precursors can be used. Those having ordinary skill in the art will understand that various other types of silane precursors may be used with the silane precursors described herein to form copolymer materials.

The polymers manufactured from the sol-gel compositions described herein can be used in optical devices. In an embodiment, the optical device comprises a polymer that includes a recurring unit of the formula (VI):

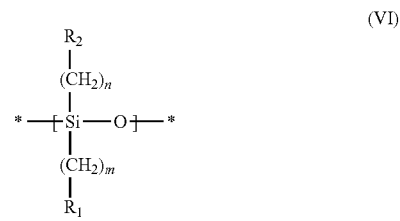

(VI)

wherein $R_1$, $R_2$, m, and n are as defined above in formula (II). In an embodiment, the optical device is in the form of a waveguide.

In an embodiment, the optical device comprises a polymer that is formed into a film. The optical device can be manufactured using wet processes, preferably those that are relatively simple and can be performed at low costs. For example, spin-coating, blade casting, or drop casting fabrication techniques can be used to manufacture an optical device comprising the polymer. Many types of optical devices, ranging from passive to active devices can be manufactured, including waveguide and electro-optic devices. System components for devices in organic electronics, such as organic light emitting diodes, solar cells, and thin film transistors can also be manufactured. In an embodiment, the polymers described herein can be used in the fabrication of one, two, and three dimensional photonic crystals using a variety of techniques, including hot embossing (nano- and micro-imprinting), ink-jet printing, and multi-photon induced polymerization.

In an embodiment, a polymer described herein comprises a recurring unit of the formula (IV) as a homopolymer. A homopolymer can be advantageous because its manufacturing process is efficiently performed using a single monomer. Additional processing steps requiring more than one container can be avoided because the polymeric material can be formed such that it contains both aromatic groups and photo-patternable groups, each of which are attached to a single monomer. A homopolymer consisting of recurring units of the formula (IV) can be produced by, for example, by polymerizing the monomer according to the formula (I) in accordance with the methods described and by using knowledge available in the art.

In another embodiment, the polymer comprising a recurring unit of the formula (IV) comprises at least one recurring unit other than that of formula (IV). For example, the polymer comprising a recurring unit of the formula (IV) can be a copolymer. Copolymerizing the monomer according to the formula (I) with other silane monomers can be useful for developing sol-gel and polymer compositions for waveguide applications. For example, other types of functional groups, such as other aromatic groups, halogenated aromatic groups, per-halogenated aromatic groups, and other photo-patternable groups can be provided. Useful monomers for polymerization and useful recurring units for incorporation into a copolymer can be found in U.S. patent application Ser. No. 12/057,828, filed on Mar. 28, 2008 and entitled "High Refractive Index Sol-gel Composition and Method of Making Photo-patterned Structures on a Substrate," the contents of which are incorporated by reference in their entirety, particularly for the purpose of describing other silane monomers that can be copolymerized with the silane monomers described herein and for the sol-gel and polymerization methods also described therein.

In an embodiment, the monomer sol-gel precursor of formula (I) can undergo a polymerization reaction to form a polymer that comprises a recurring unit of the formula (IV). In an embodiment, a monomer sol-gel precursor of formula (I) can be copolymerized with one or more of the following monomer sol-gel precursors of formulae (VII), (VIII), (IX), and/or (X):

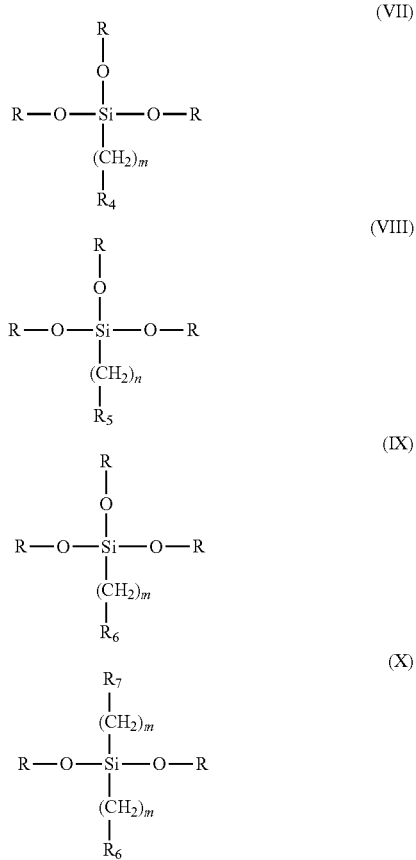

wherein $R_4$ in formula (VII) is an aromatic group substituted with at least one halogen or deuterium atom, $R_5$ in formula (VIII) is a photo cross-linkable group, each $R_6$ and $R_7$ in formulae (IX) and (X) are each independently selected to be an aromatic group selected from the group consisting of phenyl, biphenyl, naphthyl, anthracenyl, phenanthrenyl, pyrenyl, quinolinyl, tetracenyl, perylenyl, and pentacenyl, each R in formulae (VII), (VIII), (IX), and/or (X) is independently selected to be a lower alkyl group, and each m in formulae (VII), (VIII), (IX), and/or (X) is independently an integer in the range of 0 to about 10. In an embodiment, each m in formulae (VII), (IX), and/or (X) is independently an integer in the range of 0 to about 4. In an embodiment, each m in formulae (VII), (IX), and/or (X) is independently an integer in the range of 0 to about 2. In an embodiment, n in formula (VIII) is an integer in the range of 2 to about 8. In an embodiment, n in formula (VIII) is an integer in the range of 3 to about 7.

The siloxane monomers of formula (VII) that comprises $R_4$ is an example of a siloxane monomer that comprises an aromatic group substituted with at least one halogen or deuterium atom. Various types of aromatic groups may be used. For example, the aromatic group can be phenyl, biphenyl, naphthyl, anthracenyl, phenanthrenyl, pyrenyl, quinolinyl, tetracenyl, perylenyl, or pentacenyl. The aromatic group can be substituted and thus can comprise fluorine, chlorine, bromine, iodine, deuterium, or a combination thereof.

In an embodiment, the aromatic group of $R_4$ is substituted with fluorine or chlorine. In an embodiment, $R_4$ is a fluorinated aromatic group, a perfluorinated aromatic group, a brominated aromatic group, or a perbrominated aromatic group. In an embodiment, $R_4$ is a perfluorinated aromatic group or a brominated aromatic group. For example, $R_4$ can be a pentafluorophenyl group, a bispentafluorophenyl group, or a bromophenyl group. The degree of halogen or deuterium substitution on the aromatic group can vary. Any number between one hydrogen atom and all of the hydrogen atoms on an aromatic group can be substituted with a halogen atom or deuterium. For example, where the aromatic group comprises a phenyl group, the phenyl group can be substituted with one, two, three, four, or five halogen and/or deuterium atoms. In an embodiment, the aromatic group is substituted with bromine. In an embodiment, the halogenated aromatic group comprises bromoanthracenyl.

The siloxane monomer of formula (VIII) that comprises $R_5$ is a siloxane monomer that comprises a photo cross-linkable group. In an embodiment, the photo-cross-linkable group is selected from the same groups as defined above in formula (I).

The siloxane monomers $R_6$ and $R_7$ in formulae (IX) and (X) can confer high refractive index to the resulting sol-gel compositions and polymers. Each of $R_6$ and $R_7$ can be independently selected to be any aromatic group. Non-limiting examples of suitable aromatic groups include phenyl, biphenyl, naphthyl, anthracenyl, phenanthrenyl, pyrenyl, quinolinyl, tetracenyl, perylenyl and pentacenyl. In an embodiment, the aromatic group is anthracenyl. The aromatic group can be connected to the siloxane monomer, for example, by any suitable carbon atom of the aromatic group. For example, the aromatic group can be connected to the siloxane monomer, either directly or through an alkyl linker, via replacement of any hydrogen atom.

In a copolymer, the recurring unit of formula (IV) can be present in the sol-gel composition and/or polymer in any amount by varying the amounts of each monomer in the polymerization reaction. For example, in an embodiment, the mole percentage of recurring units of the formula (IV) is in the range of about 1 mol % to about 99 mol %. In an embodiment, the mole percentage of recurring units of the formula (IV) is in the range of about 10 mol % to about 95 mol %. In an embodiment, the mole percentage of recurring units of the formula (IV) is in the range of about 20 mol % to about 80 mol %. In an embodiment, the mole percentage of recurring units of the formula (IV) is in the range of about 30 mol % to about 70 mol %. In an embodiment, the mole percentage of recurring units of the formula (IV) is in the range of about 40 mol % to about 60 mol %. In an embodiment, the mole percentage of recurring units of the formula (IV) is in the range of about 30 mol % to about 50 mol %. In an embodiment, the mole percentage of recurring units of the formula (IV) is in the range of about 50 mol % to about 70 mol %. The mol % values described herein are based on the total moles of recurring units in the copolymers, as understood by those having ordinary skill in the art.

If one or more monomers of formulae (VII), (VIII), (IX), and/or (X) are added to the polymerization reaction of the monomer of formula (I), then the mol % of each recurring units of the resulting sol-gel or polymer can also be varied by adjusting the amount of monomer added.

In an embodiment, the polymer comprising a recurring unit of formula (IV) and/or the sol-gel composition comprising a recurring unit of the formula (V) further comprises one or more of the recurring units of the of (XI), (XII), (XIII), and/or (XIV):

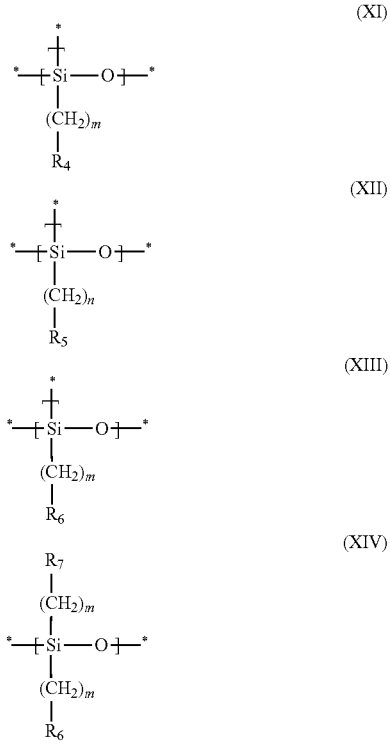

wherein $R_4$, $R_5$, each $R_6$, $R_7$, each R, and each m and n in formulae (XI), (XII), (XIII), and (XIV) is independently selected and is as defined above with regards to formulae (VII), (VIII), (IX), and (X), respectively.

The amount of recurring unit of formulae (XI), (XII), (XIII), and/or (XIV) in a sol-gel composition or a polymer can be independently selected. For example, one or more of the recurring unit of formulae (XI), (XII), (XIII), and/or (XIV) can be present in the sol-gel composition or the polymer in an amount ranging from about 0.1 mol % to about 90 mol %. In an embodiment, one or more of the recurring unit of formulae (XI), (XII), (XIII), and/or (XIV) is present in the sol-gel composition or the polymer in an amount ranging from about 0.5 mol % to about 70 mol %. In an embodiment, one or more of the recurring unit of formulae (XI), (XII), (XIII), and/or (XIV) is present in the sol-gel composition or the polymer in an amount ranging from about 1 mol % to about 50 mol %. In an embodiment, one or more of the recurring unit of formulae (XI), (XII), (XIII), and/or (XIV) is present in the sol-gel composition or the polymer in an amount ranging from about 2 mol % to about 40 mol %. In an embodiment, one or more of the recurring unit of formulae (XI), (XII), (XIII), and/or (XIV) is present in the sol-gel composition or the polymer in an amount ranging from about 5 mol % to about 30 mol %. In an embodiment, one or more of the recurring unit of formulae (XI), (XII), (XIII), and/or (XIV) is present in the sol-gel composition or the polymer in an amount ranging from about 10 mol % to about 25 mol %. In an embodiment, one or more of the recurring unit of formulae (XI), (XII), (XIII), and/or (XIV) is present in the sol-gel composition or the polymer in an amount ranging from about 25 mol % to about 50 mol %. In an embodiment, one or more of the recurring unit of formulae (XI), (XII), (XIII), and/or (XIV) is present in the sol-gel composition or the polymer in an amount ranging from about 50 mol % to about 75 mol %.

In an embodiment, a photo-initiator is added to the sol-gel composition or the polymer described herein. Any suitable photo-initiator can be used. Suitable photo-initiators accelerate curing of the composition upon activation by UV light. Non-limiting examples of photo-initiators include IRGACURE-184® (1-Hydroxy-cyclohexyl-phenyl-ketone) or IRGACURE-369® (2-Benzyl-2-dimethylamino-1-(4-morpholinophenyl)-butanone-1) (both of which are available from Ciba Specialty Chemicals). The amount of the photo-initiator can vary. In an embodiment, the photo-initiator is present in an amount in the range of about 0.1 weight % to about 10 weight % of the sol-gel composition. In an embodiment, the photo-initiator is present in an amount in the range of about 0.2 weight % to about 8 weight % of the sol-gel composition. In an embodiment, the photo-initiator is present in an amount in the range of about 0.5 weight % to about 5 weight % of the sol-gel composition.

The sol-gel compositions and polymers can be manufactured using the processes and techniques described herein, or by adaptations of such methods. In an embodiment, a polymer that is a homopolymer comprising a recurring unit of the formula (IV) or a sol-gel composition that is a homopolymer comprising a recurring unit of the formula (V) is prepared by mixing the sol-gel precursor according to formula (I) with an aqueous acidic solution. The solution can be stirred until the —OR groups of the monomer are at least partially hydrolyzed. The solution can then be cast into a film which can then be cured, e.g. polymerized, through heat and/or exposure to UV-Visible light, optionally in the presence of a photo-initiator.

In an embodiment, a sol-gel composition is prepared according to a method that comprises an initial step of mixing two or more organically modified silane precursors with an aqueous acidic solution, wherein one of the silane precursors is a monomer according to the formula (I) and at least one other silane precursor is selected from monomers according to the formulae (VII), (VIII), (IX), and/or (X). Each of the monomers described herein can be used as a sol-gel precursor.

It is also contemplated that the initial method step of producing the sol-gel may comprise mixing a single organically modified silane precursor with an aqueous acidic solution, rather than two organically modified silane precursors. For example, the silane precursor that is a monomer according to formula (IV) can be mixed alone with an aqueous acidic solution. Any one or more of the other monomers according to formulae (VII), (VIII), (IX), and/or (X) can be added thereafter, and sol-gel polymerization can be initiated.

Preferably, the monomer mixture is stirred until the —OR groups of the monomers are at least partially hydrolyzed. The solution can then be agitated (e.g., by stirring), during which the solvent can be removed in order to facilitate condensation and aging. Any monomer that is partially hydrolyzed and then agitated in the solution can participate in the reaction. In an embodiment, during or after the solvent is removed, additional solvent can be added while mixing in order to further complete hydrolysis. After this additional solvent is added, the solution is again aged, and the additional solvent is removed to form a viscous liquid. A photo-initiator can be added to the solution after, or during removal of the solvent. In an embodiment, the solvent can also be removed completely in some compositions to obtain a solid. This solid can simply be dissolved in an appropriate solvent and ready to cast films. In an embodiment, a photo-initiator can be added to the solution before casting films.

In an embodiment, the monomer according to formula (VII) is selected from the group consisting of pentafluorophenyl trimethoxysilane, bromoanthracenyl trimethoxysilane, pentafluorophenyl triethoxysilane, bromoanthracenyl triethoxysilane, and bromophenyl trimethoxysilane. In an embodiment, the monomer according to formula (VIII) is selected from the group consisting of methacryloxypropyl trimethoxysilane, methacryloxypropyl triethoxysilane, acryloxypropyl trimethoxysilane, and acryloxypropyl triethoxysilane. In an embodiment, the monomer according to formula (VIII) is methacryloxypropyl trimethoxysilane. In an embodiment, the monomer according to formulae (IX) is selected from the group consisting of anthracenyl trimethoxysilane, phenanthrenyl triethoxysilane, naphthyl trimethoxysilane, pyrenyl trimethoxysilane, and perylenyl triethoxysilane. In an embodiment, the monomer according to formula (IX) comprises perylenyl 3,9-bis(triethoxysilane). In an embodiment, the monomer according to formula (IX) is selected from 1-trimethoxysilylanthracene, 2-trimethoxysilylanthracene, 9-trimethoxysilylanthracene, and combinations thereof. In an embodiment, the monomer according to formula (IX) is 9-trimethoxysilylanthracene.

The monomers according to formulae (VII), (VIII), and (IX) are compounds having three alkoxy groups attached to a silicon atom with a single mono-substitution on the silicon atom of an $R_4$, $R_5$, and $R_6$ group, respectively. However, it is additionally contemplated that di- and tri-substituted alkoxysilane groups can also be used. For example, the monomer of formula (X) is a di-substituted variation of the monomer of formula (IX). Non-limiting examples of the monomer according to formula (X) include bis(pyrenyl) dimethoxysilane and bis(pyrenyl) diethoxysilane. Alkoxysilane monomers that are di-substituted with halogenated aromatic groups are known. Non-limiting examples of such compounds include bispentafluorophenyl dimethoxysilane and bispentafluorophenyl diethoxysilane.

Each of the monomers described herein can exist in various isomeric forms. In particular, monomers containing aromatic groups, whether substituted or unsubstituted, can have the aromatic group bonded to the silicon atom, either directly or by a linker, at any number of carbon positions on the aromatic group. Selection of a particular isomer can depend upon several factors, including ease of synthesis of the monomer. Those having ordinary skill in the art, guided by the disclosure herein, will understand that each of the isomers is contemplated as usable herein.

The sol-gel compositions and polymers described herein can be used to form photo-patterned structures on substrates. In an embodiment, a method of making photo-patterned structures on a substrate is provided, the method comprising the initial step of coating a sol-gel on at least a portion of the substrate to form a film, wherein the sol-gel comprises a recurring unit of the formula (IV), as described above. After the sol-gel film has been coated, it can be soft baked at a low temperature to remove solvent. As used herein, the term "soft bake" refers to a heating operation with the purpose of evaporating at least a portion of the solvents in the sol-gel film, wherein the heating conditions are at a low enough temperature and time duration such that the sol-gel film does not harden to an inflexible degree and remains soft.

The sol-gel film can then be masked. The mask is positioned over the sol-gel film and preferably has at least one opening to define a pattern design. Any suitable masking technique and masking material can be used to apply the mask. The mask protects covered areas of the sol-gel film from radiation by light. Uncovered areas, e.g. areas of the sol-gel that are adjacent to the openings in the mask can be exposed to light and rendered insoluble by the radiation.

After the mask is positioned and a desired outline of a pattern created, at least a portion of the uncovered area of the sol-gel film can then be exposed to ultra-violet (UV) radiation through at least one opening in the mask to render the exposed portion of the film insoluble to a selected solvent through the full thickness of the film. The sol-gel film can then be washed in the selected solvent to remove, e.g. by dissolving, the unexposed portion of the film. The dissolved portion of the sol-gel film can then be removed, thus leaving behind a desired sol-gel film pattern. The remaining sol-gel film pattern can be hardened by hard baking the film at a higher temperature in a vacuum oven. Hard baking can also further remove any solvent left over from the soft baking step. As used herein, the term "hard bake" means a heating operation at sufficient time and temperature to achieve further polymerization of the sol-gel material and adhesion of the sol-gel material to the substrate.

Various types of substrates may be used to form the photo-patterned structures thereon. In an embodiment, the substrate comprises a silicon wafer. Silicon wafers can be provided with buffer layers before the sol-gel composition is formed on the substrate. In an embodiment, the silicon wafer comprises a $SiO_2$ buffer layer. The buffer layer may be thermally grown on the substrate to any desired degree of thickness. For example, the buffer layer can have a thickness in the range of about 3 μm to about 20 μm. In an embodiment, the buffer layer has a thickness in the range of about 4 μm to about 10 μm. In an embodiment, the buffer layer has a thickness in the range of about 10 μm to about 15 μm. In an embodiment, the buffer layer has a thickness in the range of about 16 μm to about 20 μm.

Additional layers may be provided on top of the silicon wafer in addition to the buffer layer. In an embodiment, silicon wafer further comprises a metal layer over (e.g., on) the $SiO_2$ buffer layer. Useful metal layers include, but are not limited to Au, Ag, Cu, Ti, Al, Cr, Mo, and combinations and alloys thereof. The sol-gel composition can be deposited over the silicon wafer, over the buffer layer, or over the metal layer on top of the buffer layer.

The substrate can also comprise glass and/or quartz. The glass may also have additional buffer and/or metal layers of varying thicknesses. In an embodiment, the glass further comprises a metal layer. In an embodiment, the metal layer deposited over the glass is selected from Ti, Al, Cr, or Mo. In an embodiment, the metal layer deposited over the glass is molybdenum.

The thickness of the metal layer deposited over the glass can vary. In an embodiment, the metal layer deposited over the glass has a thickness in the range of about 50 nm to about 700 nm. In an embodiment, the metal layer deposited over the glass has a thickness in the range of about 200 nm to about 500 nm. In an embodiment, the metal layer deposited over the glass has a thickness in the range of about 50 nm to about 150 nm. In an embodiment, the metal layer deposited over the glass has a thickness in the range of about 150 nm to about 250 nm. In an embodiment, the metal layer deposited over the glass has a thickness in the range of about 250 nm to about 350 nm. In an embodiment, the metal layer deposited over the glass has a thickness in the range of about 350 nm to about 450 nm. In an embodiment, the metal layer deposited over the glass has a thickness in the range of about 450 nm to about 550 nm. In an embodiment, the metal layer deposited over the glass has a thickness in the range of about 550 nm to about 700 nm.

An embodiment is a method of making photo-patterned structures on a substrate. The manufacturing steps of making a photo-patterned structure on a substrate can comprise the steps of (a) coating a sol-gel on at least a portion of the substrate to form a film, wherein the sol-gel comprises a recurring unit of the formula (I); (b) soft baking the film to form a sol-gel film; (c) positioning a mask over the sol-gel film, wherein the mask comprises at least one opening that defines a pattern design; (d) exposing at least a portion of the sol-gel film to ultra-violet radiation through the at least one opening in the mask to create an unexposed portion of the film and an exposed portion of the film, wherein the exposed portion of the film is insoluble to a selected solvent through the full thickness of the film; (e) removing the unexposed portion of the film by washing it with the selected solvent; and (f) hard baking the film at a reduced pressure.

Synthesis of Sol-Gel Precursor Monomers

The following synthesis methods can be used in the manufacture of the sol-gel precursors. All NMR data was obtained on a JEOL Eclipse+400 FT NMR Spectrometer. MS was conducted on a Thermo Finnigan LCQdeca Mass Spectrometer using electrospray ionization positive ion mode.

Synthesis A:
γ-(methacryloxy)propylphenyldiethoxysilane (B)

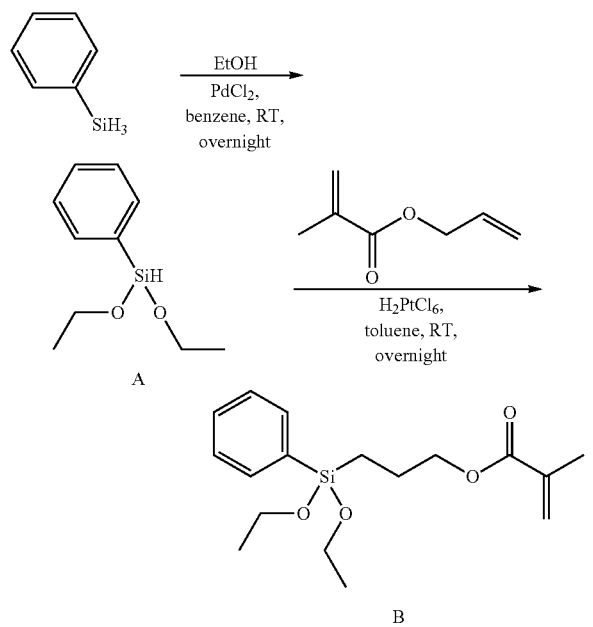

A

B

Phenylsilane in an amount of about 8.74 g (80.9 mmol) was weighed into a reaction flask and about 210 mL of dry degassed benzene was added via cannula under argon. The solution was then further degassed for about 5 minutes by bubbling argon through it. A suspension of about 14.2 mg (0.1 mol %) of PdCl2 in a small amount of benzene was then added, causing the solution to become dark. Dry absolute ethanol in an amount of about 7.44 g (161 mmol) was added via a syringe which caused vigorous bubbling to occur. The reaction was then stirred overnight at room temperature (~17° C.). See Ohshita et al., *J. Organometallic Chem.*, 689 (2004), 3258-3264. The yield of the diethoxyphenylsilane (A) was about 10.5 g (66%).

Diethoxyphenylsilane in an amount of about 500 mg (2.55 mmol) was weighed into a reaction flask. In a separate flask, about 290 mg (2.30 mmol) of allyl methacrylate was weighed and about 1 mL of degassed toluene was added. This solution was transferred to the reaction flask containing the diethoxyphenylsilane and rinsed with an additional 1 mL of toluene. This solution was degassed for 5 minutes by bubbling argon through it, and then about 46 μL, of a 5 mg/mL solution of $H_2PtCl_6$ in tetrahydrofuran was added. See European Patent App. Pub. No. 0277023 to Shiozawa et al. The reaction was stirred overnight at room temperature. The reaction mixture was evaporated at 30° C. and subsequently purified by column chromatography using 2:1 methylene chloride:hexane on silica gel. Evaporating all relevant fractions afforded a colorless liquid.

The yield of γ-(methacryloxy) propylphenyldiethoxysilane (B) was about 600 mg (73%). The $^1$H-NMR data was as follows (400 MHz, CDCl$_3$): δ=7.61 (m; 2H), 7.45-7.32 (m; 3H), 6.07 (s; 1H), 5.52 (s; 1H), 4.10 (t; 2H), 3.82 (q; 4H), 1.92 (s; 3H), 1.73 (m; 2H), 1.25 (t; 6H), 0.88 (m; 2H). MS: m/z 323 (M$^+$). n$_D^{25}$ 1.4828.

Synthesis B: γ-(methacryloxy)propyl(2-naphthyl)diethoxysilane (E)

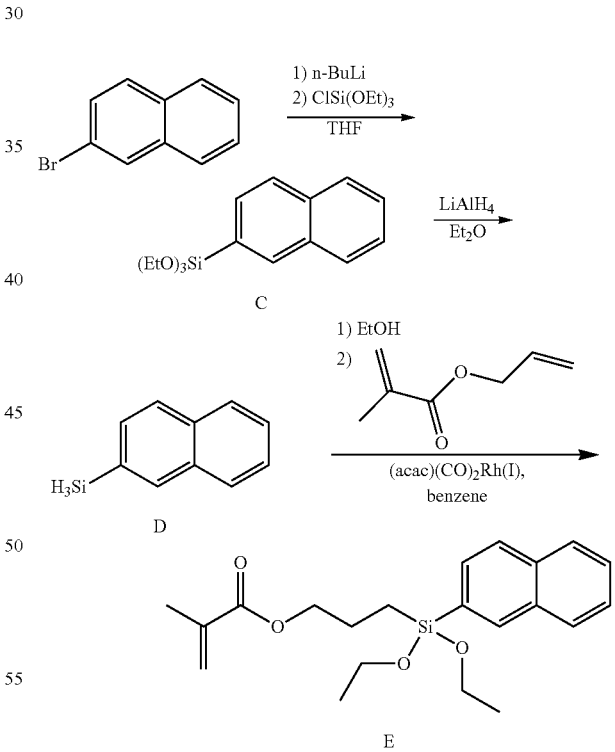

E

A solution of 2-bromonaphthalene (about 8.4 g, 40.6 mmol) in tetrahydrofuran (about 50 mL) was cooled to −78° C. under argon was prepared. Then, n-butyllithium (about 42.2 mmol) was added dropwise. This solution was stirred for 1.5 hours at −78° C. before chlorotriethoxysilane (about 24 g, 122 mmol) was added in one quick shot via syringe. This solution was allowed to warm to room temperature naturally and was stirred for 1.5 hours.

The reaction mixture was added to a separatory funnel containing ice-cold diethyl ether and water containing NaOH (about 81.2 mmol). The organic phase was washed with ice-cold brine, dried with Na$_2$SO$_4$, and then evaporated. The crude product was further purified via silica gel column chromatography with 3:2 hexane:dichloromethane to yield a colorless oil. The yield of (2-naphthyl)triethoxysilane (C) was about 10.5 g (89%). The $^1$H-NMR data was as follows (400 MHz, C$_2$D$_2$Cl$_4$): δ=8.19 (s; 1H), 7.90 (d; J=8.8 Hz; 1H), 7.84 (d; J=8.4 Hz; 2H), 7.70 (d; J=8.1 Hz; 1H), 7.52 (m; 2H), 3.87 (q; 6H), 1.24 (t; 9H).

A solution of (2-naphthyl)triethoxysilane (about 20.3 g, 70 mmol) in diethyl ether (about 100 mL) was added via addition funnel to a suspension of ice-cold LiAlH$_4$ (about 5.5 g, 145 mmol) in diethyl ether (about 100 mL). The reaction mixture was warmed to room temperature and stirred overnight. The solids were filtered and the filtrate evaporated to yield a white solid. This solid was taken up in dichloromethane and quickly plug filtered through silica gel to remove inorganic salts. A white solid was obtained.

The yield of (2-naphthyl)silane (D) was about 10.5 g (95%). The $^1$H-NMR data was as follows (400 MHz, C$_2$D$_2$Cl$_4$): δ=8.13 (s; 1H), 7.83 (m; 3H), 7.63 (dd; J$_1$=8.4 Hz, J$_2$=1.1 Hz; 1H), 7.52 (m; 2H), 4.33 (s; 3H). See Riedmiller et al., *Organometallics*, 17, 4444-4453 (1998).

To a degassed solution of (2-naphthyl)silane (about 7.57 g, 47.9 mmol) and (acetylacetonato)dicarbonylrhodium(I) (about 134 mg, 1 mol %) in benzene (about 134 mL), absolute anhydrous ethanol (about 4.41 g, 47.9 mmol) was added via a syringe. After stirring for 1.25 hours, a solution of allyl methacrylate (about 6.16 g, 48.9 mmol) in benzene (about 5 mL) was added dropwise over 30 minutes. During the course of this addition, the reaction flask was placed in a room temperature water bath to moderate the reaction temperature. The reaction was allowed to stir at room temperature for 1.25 hours. The reaction mixture was added directly to a column containing silica gel packed with toluene. After the first byproduct finished eluting, dichloromethane was added to elute the product. The product was a faint yellow oil.

The yield of the γ-(methacryloxy)propyl(2-naphthyl)diethoxysilane (E) was about 6.1 g (36%). The $^1$H-NMR data was as follows (400 MHz, CDCl$_3$): δ=8.15 (s; 1H), 7.83 (m; 3H), 7.67 (d; J=8.1 Hz; 1H), 7.50 (m; 2H), 6.06 (s; 1H), 5.51 (s; 1H), 4.08 (t; 2H), 3.87 (q; 4H), 1.91 (s; 3H), 1.75 (m; 2H), 1.28 (t; 6H), 0.96 (m; 2H). See Murata et al., *Tetrahedron*, 63, 4087-4094 (2007) and European Patent App. Pub. No. 0277023 to Shiozawa et. al. MS: m/z 373 (M$^+$). n$_D^{25}$ 1.5324.

Synthesis C: γ-(methacryloxy)propyl(1-pyrenyl)diethoxysilane (H)

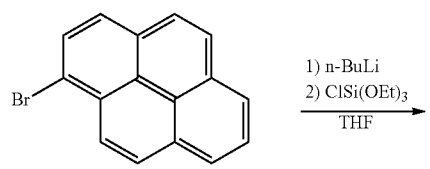

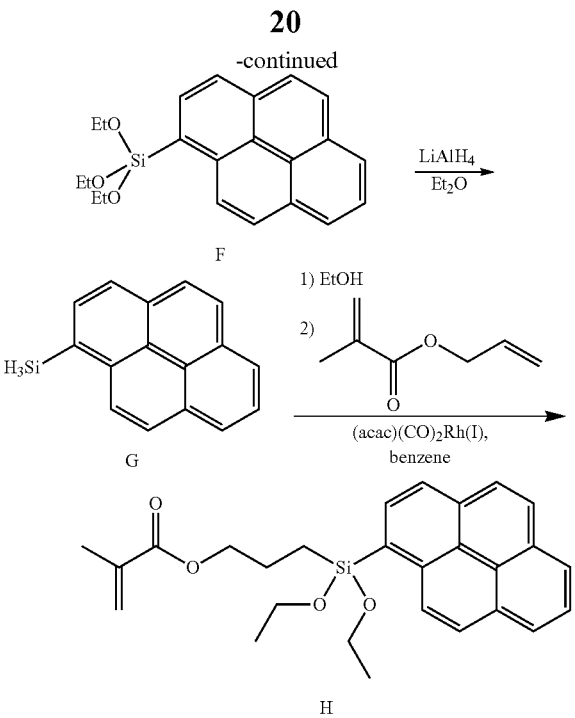

All glassware used in the reaction was oven dried before use. To a 50 ml single-neck round-bottom flask was added about 3.29 g (11.7 mmol) of bromopyrene. The flask was stoppered with a rubber septum and evacuated via a vacuum line adapted to a syringe needle. After removing the needle quickly, THF was cannulated into the reaction flask via a double-ended needle until the starting material dissolved (about 35-40 mL). A balloon charged with argon was used to introduce an inert atmosphere. This solution was cooled to −78° C. and about 8.0 mL (12.7 mmol) of n-butyllithium in hexanes was added dropwise over about 5 minutes. See Beinhoff et al., *Eur. J. Org. Chem.*, 2001, 3819-3829. The yellow suspension was stirred at −78° C. for 40 minutes and then about 10 g (50.3 mmol) of triethoxychlorosilane, freshly distilled from CaH$_2$, was added in one shot via syringe. See co-pending U.S. patent application Ser. No. 12/057,828 to Kathaperumal, et al. The color dissipated and solids went into solution immediately. The reaction mixture was warmed naturally to room temperature and stirred overnight (though the reaction was nearly complete within minutes).

The excess triethoxychlorosilane was quenched by treatment with about 10 ml absolute anhydrous ethanol, and the solvents were subsequently removed via rotory evaporation. The resultant oil was taken up in about 25 mL of the elution solvent, filtered to remove LiBr, and added to a column containing a copious amount of silica gel. The column was eluted using 1:1 hexane:dichloromethane (R$_f$ 0.5) and evaporated to yield a faint yellow oil. The yield of (1-pyrenyl)triethoxysilane (F) was about 2.7 g (63%). The $^1$H-NMR data was as follows (400 MHz, 1,1,2,2-tetrachloroethane): δ=8.61 (d; J=9.1 Hz; 1H), 8.47 (d; J=7.7 Hz; 1H), 8.24-8.04 (m; 7H), 3.90 (q; 6H), 1.26 (t; 9H).

A solution of (1-pyrenyl)triethoxysilane (about 6.54 g, 17.9 mmol) in diethyl ether (about 30 mL) was added via addition funnel to a suspension of ice-cold LiAlH$_4$ (about 470 mg, 11.8 mmol) in diethyl ether (about 45 mL). The reaction mixture was warmed to room temperature and stirred overnight. See Riedmiller et al., *Organometallics*, 1998, 17, 4444-4453 and Minge et al., *Organometallics*, 2002, 21, 680-684. The solids were filtered and the filtrate evaporated to yield a white solid. The solid was taken up in dichloromethane and quickly plug filtered through silica gel to remove inorganic salts. A fluorescent white solid was obtained. The yield of (1-pyrenyl)silane (G) was about 3.2 g (77%). The $^1$H-NMR data was as follows (400 MHz, $C_2D_2Cl_4$): δ=8.31-8.03 (m; 9H), 4.68 (s; 3H).

To a degassed solution of (1-pyrenyl)silane (about 10.33 g, 44.5 mmol) and (acetylacetonato)dicarbonylrhodium(I) (about 116 mg, 1 mol %) in benzene (about 125 mL), absolute anhydrous ethanol (about 4.11 g, 89 mmol) was added dropwise in 1 mL portions via syringe over 1.5 hours at 10° C. The reaction was warmed to room temperature and monitored by NMR, and after stirring an additional 1.5 hours, appeared to be complete. Allyl methacrylate (about 2.85 g, 22.6 mmol) was then added dropwise via syringe in 0.5 mL portions over 15 minutes at 10° C. and stirred for one hour. Another portion of allyl methacrylate (about 2.84 g, 22.5 mmol) was added under similar conditions. The reaction was allowed to warm to room temperature naturally and stirred another 2 hours, monitoring by NMR. See Murata et al., *Tetrahedron*, 63, 4087-4094 (2007) and European Patent App. Pub. No. 0277023 to Shiozawa et al.

The reaction mixture was added directly to a chromatography column packed with silica gel and eluted with toluene to yield a viscous amber oil. The yield of γ-(methacryloxy)propyl(1-pyrenyl)diethoxysilane (H) was about 7.87 g (40%). The $^1$H-NMR data was as follows (400 MHz, $CDCl_3$): δ=8.59 (d; J=9.1 Hz; 1H), 8.43 (d: J=7.7 Hz; 1H), 8.22-8.00 (m; 7H), 5.98 (s; 1H), 5.43 (s; 1H), 4.04 (t; 2H), 3.92 (q; 4H), 1.84 (s; 3H), 1.74-1.69 (m; 2H), 1.31 (t; 6H), 1.16-1.11 (m; 2H). MS: m/z 464 [M+$NH_4$]$^+$. $n_D^{25}$ 1.6157.

Synthesis D: γ-(methacryloxy)propyl(9-phenanthrenyl)diethoxysilane (L)

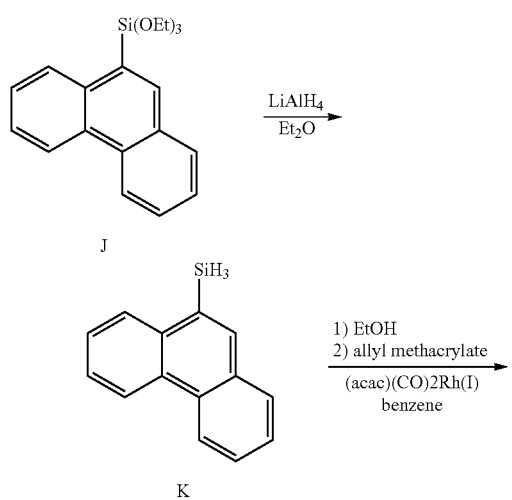

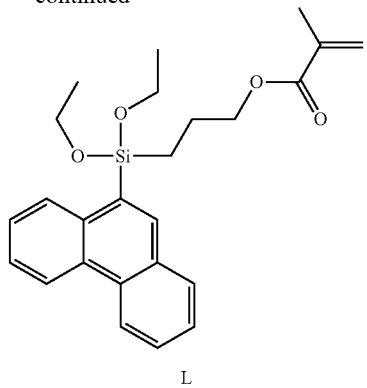

Compound J was prepared in accordance with the conditions shown for Compound C, except that 9-bromophenanthrene was used for a starting ingredient instead of 2-bromonaphthalene. A faint yellow oil was present as the resulting product. The yield of (9-phenanthrenyl)triethoxysilane) (J) was about 15 g (36%). The $^1$H-NMR data was as follows (400 MHz, $CDCl_3$): δ=8.72 (dd; $J_1$=7.7 Hz, $J_2$=1.8 Hz; 1H), 8.71 (d; J=8.4 Hz; 1H), 8.40 (dd; $J_1$=7.7 Hz, $J_2$=1.8 Hz; 1H), 8.32 (s; 1H), 7.93 (dd; $J_1$=8.1 Hz, $J_2$=1.5 Hz; 1H), 7.74-7.58 (m; 4H), 3.94 (q; 6H), 1.27 (t; 9H).

$LiAlH_4$ (520 mg, 13.7 mmol) was added portion-wise to a solution of (9-phenanthrenyl)triethoxysilane (4.04 g, 11.9 mmol) in diethyl ether (50 mL) at 0° C. Once the reaction was complete, hexane (50 mL) was added to precipitate the salts and the reaction mixture was filtered. The filtrate was concentrated by rotary evaporation. The residue was taken up in dichloromethane and plug filtered through silica gel. The product was concentrated by rotary evaporation to yield a white solid. The yield of 9-phenanthrenylsilane (K) was about 2.26 g (91%). The $^1$H-NMR data was as follows (400 MHz, $CDCl_3$): δ=8.72 (d; J=7.3 Hz; 1H), 8.68 (d; J=8.4 Hz; 1H), 8.15 (s; 1H), 7.98 (d; J=7.3 Hz; 1H), 7.88 (d; J=7.7 Hz; 1H), 7.77-7.57 (m; 4H), 4.52 (s; 3H).

A solution of 9-phenanthrenylsilane (2.1 g, 10.2 mmol) and (acac)(CO)$_2$Rh(I) (30 mg, 1.15 mol %) in degassed benzene (30 mL) was prepared, to which anhydrous absolute ethanol (844 mg, 18.4 mmol) was added in 4 equal portions over 2 hours. The bubbling was stopped, and the reaction mixture was degassed for 10 minutes by bubbling Argon gas through it. Afterwards, another portion of (acac)(CO)$_2$Rh(I) (20 mg, 0.78 mol %) was added, followed by allyl methacrylate (1.29 g, 10.2 mmol), which was added in three equal portions over 1 hour.

Once the reaction was complete (monitored by NMR), the reaction mixture was added to and eluted through a column of silica gel via a 1:1 hexane:dichloromethane to 100% dichloromethane gradient to yield a slightly amber oil. The yield of γ-(methacryloxy)propyl(9-phenanthrenyl)diethoxysilane (K) was bout 1.25 g (28%). The $^1$H-NMR data was as follows (400 MHz, $CDCl_3$): δ=8.73 (dd; $J_1$=7.3 Hz, $J_2$=1.5 Hz; 1H), 8.68 (d; J=8.4 Hz; 1'-1), 8.35 (dd; $J_1$=7.7 Hz, $J_2$=1.5 Hz; 1H), 8.25 (s; 1H), 7.93 (d; J=7.7 Hz; 1H), 7.72-7.57 (m; 4H), 6.00 (s; 1H), 5.47 (s; 1H), 4.05 (t; 2H), 3.91 (q; 4H), 1.87 (s; 3H), 1.70 (m; 2H), 1.29 (t; 6H), 1.08 (m; 2H). $n_D^{25}$ 1.5784.

EXAMPLES

Example 1

A sol-gel composition was prepared by mixing about 1 g of γ-(methacryloxy)propyl(1-pyrenyl)diethoxysilane (H), about 2 g of tetrahydrofuran, and about 0.500 g of aqueous (0.01N) HCl and stirring the resulting mixture for about 12 hours at ambient conditions. The solution was aged for a few hours at room temperature prior to spin coating. The spin-coated film was cured at about 150° C. for about 2 hours in an oven.

Example 2

A sol-gel composition was prepared by mixing about 1 g of γ-(methacryloxy)propyl(1-pyrenyl)diethoxysilane (H), about 2 g of Tetrahydrofuran, and about 0.500 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone (Irgacure 369) was added in an amount of about 0.020 g to the mixture and the solution stirred for about 1 hour prior to spin coating. The spin-coated film was cured with UV light at 365 nm for about 3 minutes. The UV exposed film was then further developed in 2-propanol (solvent) and dried at room temperature.

Example 3

A sol-gel composition was prepared by mixing about 1 g of γ-(methacryloxy)propyl(1-pyrenyl)diethoxysilane (H), about 2 g of Tetrahydrofuran, and about 0.500 g of aqueous (0.01N) HCl and stirring the resulting mixture for about 12 hours at ambient conditions. The solution was aged for a few hours at room temperature. Then, the photo-initiator 2-hydroxy-1-[4-(2-hydroxyethoxy)phenyl]-2-methyl-1-propanone (Irgacure 2959) was added in an amount of about 0.020 g to the mixture and the solution stirred for about 1 hour prior to spin coating. The spin-coated film was cured with UV light at 365 nm for about 3 minutes. The UV exposed film was then further developed in 2-propanol (solvent) and dried at room temperature.

Example 4

A sol-gel composition was prepared by mixing about 1 g of γ-(methacryloxy)propyl(1-pyrenyl)diethoxysilane (H), about 0.3589 g of pentafluorophenyl trimethoxysilane, about 0.9690 g of bis-pyrenyldimethoxysilane, about 4 g of tetrahydrofuran, and about 0.5136 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone was added in an amount of about 0.5473 g to the mixture and the solution stirred for about 1 hour prior to spin coating. The spin-coated film was cured with UV light at 365 nm for about 3 minutes. The UV exposed film was then further developed in 2-propanol (solvent) and dried at room temperature.

Example 5

A sol-gel composition was prepared by mixing about 1 g of γ-(methacryloxy)propyl(2-naphthyl)diethoxysilane (E), about 2 g of tetrahydrofuran, and about 0.500 g of aqueous (0.01N) HCl and stirring the resulting mixture for about 12 hours at ambient conditions. The solution was aged for a few hours at room temperature prior to spin coating. The spin-coated film was cured at about 150° C. for about 2 hours in an oven.

Example 6

A sol-gel composition was prepared by mixing about 1 g of γ-(methacryloxy)propyl(2-naphthyl)diethoxysilane (E), about 2 g of tetrahydrofuran, and about 0.500 g of aqueous (0.01N) HCl and stirring the resulting mixture for about 12 hours at ambient conditions. The solution was aged for a few hours at room temperature. The photo-initiator 2-benzyl-2-(dimethylamino)-1-[4-(4-morpholinyl)phenyl]-1-butanone (Irgacure 369) was added in an amount of about 0.020 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 7

A sol-gel composition was prepared by mixing about 1 g of γ-(methacryloxy)propyl(2-naphthyl)diethoxysilane (E), about 2 g of tetrahydrofuran, and about 0.500 g of aqueous (0.01N) HCl and stirring the resulting mixture for about 12 hours at ambient conditions. The solution was aged for a few hours at room temperature. Then, the photo-initiator 2-benzyl-2-(1-hydroxy-cyclohexylphenylketone (Irgacure 184) was added in an amount of about 0.020 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 8

A sol-gel composition was prepared by mixing 1 g of γ-(methacryloxy)propyl(2-naphthyl)diethoxysilane (V), 0.3108 g of pentafluorophenyltrimethoxysilane, 0.8391 g of bis-pyrenyldiethoxysilane, 4 g of tetrahydrofuran and 0.4447 g of aqueous (0.01N) HCl and stirring the resulting mixture for 12 hours at ambient conditions. The solution was aged for a few hours at room temperature. Then, the photo-initiator 2-benzyl-2-(dimethylamino)-1-[4-(4-morpholinyl)phenyl]-1-butanone in an amount of 0.5275 g was added to the mixture and the solution stirred for 1 hr prior to spin coating. The spin-coated film was cured with UV light at 365 nm for about 3 minutes. The UV exposed film was then further developed in 2-propanol (solvent) and dried at room temperature.

Example 9

A sol-gel composition was prepared by mixing about 1 g of γ-(methacryloxy)propyl(2-naphthyl)diethoxysilane (E), about 0.1942 g of pentafluorophenyl trimethoxysilane, about 1 g of tetrahydrofuran, and about 0.530 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone was added in an amount of about 0.2179 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 10

A sol-gel composition was prepared by mixing about 1 g of γ-(methacryloxy)propyl(2-naphthyl)diethoxysilane (E), about 0.333 g of pentafluorophenyl trimethoxysilane, about 1 g of tetrahydrofuran, and about 0.530 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone was added in an amount of about 0.229 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 11

A sol-gel composition was prepared by mixing about 1 g of γ-(methacryloxy)propyl(phenyl)diethoxysilane (B), about 0.3589 g of pentafluorophenyl trimethoxysilane, about 0.9690 g of bis-pyrenyldiethoxysilane, about 4 g of tetrahydrofuran, and about 0.5136 g of aqueous (0.01N) HCl and stirring the resulting mixture for about 12 hours at ambient conditions. The solution was aged for a few hours at room temperature prior to spin coating. The spin-coated film was cured at about 150° C. for about 2 hours in an oven.

Example 12

A sol-gel composition was prepared by mixing about 1 g of γ-(methacryloxy)propylphenyldiethoxysilane (B), about 2 g of tetrahydrofuran, and about 0.500 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone (Irgacure 369) was added in an amount of about 0.020 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 13

A sol-gel composition was prepared by mixing about 1 g of γ-(methacryloxy)propyl(phenyl)diethoxysilane (B), about 0.3589 g of pentafluorophenyl trimethoxysilane, about 0.9690 g of bis-pyrenyldiethoxysilane, about 4 g of tetrahydrofuran, and about 0.5136 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone was added in an amount of about 0.5473 g to the mixture and the solution stirred for 1 hour prior to spin coating. The spin-coated film was cured with UV light at 365 nm for about 3 minutes. The UV exposed film was then further developed in 2-propanol (solvent) and dried at room temperature.

Example 14

A sol-gel composition was prepared by mixing about 1 g of γ-(methacryloxy)propyl(phenyl)diethoxysilane (B), about 0.2248 g of pentafluorophenyl trimethoxysilane, about 1 g of tetrahydrofuran, and about 0.088 g of aqueous (0.01N) HCl and stirring the resulting mixture for about 12 hours at ambient conditions. The solution was aged for a few hours at room temperature prior to spin coating. The spin-coated film was cured at about 150° C. for about 2 hours in an oven.

Example 15

A sol-gel composition was prepared by mixing about 1 g of γ-(methacryloxy)propyl(phenyl)diethoxysilane (B), about 0.598 g of pentafluorophenyl trimethoxysilane, about 1 g of tetrahydrofuran, and about 0.148 g of aqueous (0.01N) HCl and stirring the resulting mixture for about 12 hours at ambient conditions. The solution was aged for a few hours at room temperature. Then, the photo-initiator 2-benzyl-2-(dimethylamino)-1-[4-(4-morpholinyl)phenyl]-1-butanone was added in an amount of about 0.20 g to the mixture and the solution stirred for 1 hr prior to spin coating. The spin-coated film was cured with UV light at 365 nm for about 3 minutes. The UV exposed film was then further developed in 2-propanol (solvent) and dried at room temperature.

Refractive Index

The refractive index of each of the various sol-gel compositions provided above in the examples was measured using a Metricon Prism coupler. The sols were spin-coated onto silicon wafers at 1000 rpm over about 45 seconds and formed into film. This is a standard method used for refractive index evaluation of thin films at 633 and 1550 nm. Results of the refractive index measurements are given in Table 1. A refractive index was not measured in the case of Example 12 because the film was not completely cured under these conditions.

The numbers and percentages indicated in Table 1 represent the mol percentage of the monomer precursor that forms the recurring unit in the sol-gel.

TABLE 1

Refractive Index Results

| Example | Sol-gel composition | Refractive Index (at 633 nm) | Refractive Index (at 1550 nm) |
|---|---|---|---|
| 1 | PyrAIO(100%) | 1.6641 | 1.6267 |
| 2 | PyrAIO(100%) | N/A | N/A |
| 3 | PyrAIO(100%) | N/A | N/A |
| 4 | BpyrDES(30%) + PFPh(20%) + PyrAIO(50%) | 1.6974 | 1.6537 |
| 5 | NaAIO(100%) | 1.6015 | 1.5761 |
| 6 | NaAIO(100%) | N/A | N/A |
| 7 | NaAIO(100%) | N/A | N/A |
| 8 | NaAIO (50%) + BpyrDES(30%) + PFPhTMS(20%) | 1.6642 | 1.6267 |
| 9 | NaAIO(80%) + PFPhTMS(20%) | 1.5805 | 1.5575 |
| 10 | NaAIO(70%) + PFPhTMS(30%) | 1.5744 | 1.5543 |
| 11 | PhAIO(50%) + BpyrDES(30%) + PFPhTMS(20%) | 1.6609 | 1.6230 |
| 12 | PhAIO(100%) | N/A | N/A |
| 13 | PhAIO(50%) + BpyrDES(30%) + PFPhTMS(20%) | 1.6232 | 1.6530 |
| 14 | PhAIO(80%) + PFPhTMS(20%) | 1.5285 | 1.5126 |
| 15 | PhAIO(60%) + PFPhTMS(40%) | 1.5201 | 1.5042 |

PhAIO: γ-(methacryloxy)propyl(phenyl)diethoxysilane (Compound B)
NaAIO: γ-(methacryloxy)propyl(2-naphthyl)diethoxysilane (Compound E)
PyrAIO: γ-(methacryloxy)propyl(1-pyrenyl)diethoxysilane (Compound H)
BpyrDES: bis(pyrenyl)diethoxysilane
PFPhTMS: pentafluorophenyl trimethoxysilane

What is claimed is:

1. A sol-gel precursor comprising a monomer according to the formula (I):

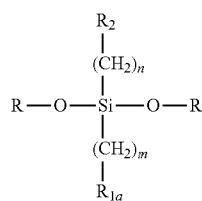

(I)

wherein $R_{1a}$ is an optionally substituted aromatic group, wherein the aromatic group is selected from the group consisting of biphenyl, naphthyl, anthracenyl, phenanthrenyl, quinolinyl, tetracenyl, pentacenyl, pyrenyl, and perylenyl; $R_2$ is a photo-cross-linkable group comprising at least one of a methacrylate group, an acrylate group, an alkenyl group, a vinyl group, an epoxy group, or an acryloxy group; each R is independently selected to be a lower alkyl group or a lower alkoxyalkyl group; m is selected to be an integer in the range of 0 to about 10; and n is selected to be an integer in the range of 2 to about 10.

2. The sol-gel precursor of claim 1, wherein m is 0.
3. The sol-gel precursor of claim 1, wherein n is an integer in the range of 3 to 7.
4. The sol-gel precursor of claim 1, wherein n and $R_2$ in formula (I) are selected such that $-(CH_2)_n-R_2$ is a propylmethacrylate group, a propylacrylate group, or an epoxypropyl group.
5. The sol-gel precursor of claim 1, wherein the monomer is selected from the group consisting of γ-(methacryloxy)propyl(2-naphthyl)diethoxysilane and γ-(methacryloxy)propyl(1-pyrenyl)diethoxysilane.
6. The sol-gel precursor of claim 1, wherein the refractive index of the monomer of the formula (I) is greater than 1.45 when measured at 589 nm.
7. A method of making a sol-gel precursor of the formula (II):

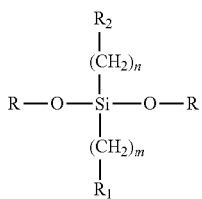

(II)

wherein $R_1$ is an optionally substituted aromatic group, wherein the aromatic group is selected from the group consisting of phenyl, biphenyl, naphthyl, anthracenyl, phenanthrenyl, quinolinyl, tetracenyl, pentacenyl, pyrenyl, and perylenyl; $R_2$ is a photo-cross-linkable group comprising at least one of a methacrylate group, an acrylate group, an alkenyl group, a vinyl group, an epoxy group, or an acryloxy group; each R is independently selected to be a lower alkyl group or a lower alkoxyalkyl group; m is selected to be an integer in the range of 0 to about 10; and n is selected to be an integer in the range of 2 to about 10;
the method comprising the steps of:
providing a solution that comprises a compound having a structure according to the formula (III):

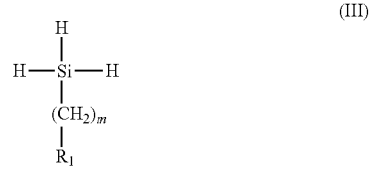

(III)

wherein $R_1$ and m are as defined above in formula (II);
intermixing a transition metal catalyst with said solution;
intermixing a compound having the formula R—OH with said solution, wherein R is as defined above in formula (II); and
intermixing a compound having the formula $R_2-(CH_2)_{n-2}-CH=CH_2$ with said solution, wherein $R_2$ and n are as defined above in formula (II).

8. The method of claim 7, wherein the transition metal catalyst is a single transition metal catalyst.
9. The method of claim 8, wherein the single transition metal catalyst is capable of catalyzing dehydrogenative coupling of the compound having the formula R—OH to an organosilane.
10. The method of claim 8, wherein the single transition metal catalyst is capable of catalyzing the coupling of the terminal olefin in the compound having the formula $R_2-(CH_2)_{n-2}-CH=CH_2$ to an organodialkoxysilane.
11. The method of claim 8, wherein the single transition metal catalyst comprises (acetylacetonato)dicarbonylrhodium(I).
12. A polymer comprising a recurring unit of the formula (IV):

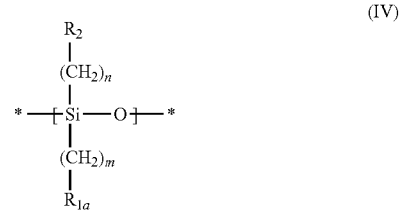

(IV)

wherein
$R_{1a}$ is an optionally substituted aromatic group, wherein the aromatic group is selected from the group consisting of biphenyl, naphthyl, anthracenyl, phenanthrenyl, quinolinyl, tetracenyl, pentacenyl, pyrenyl, and perylenyl;
$R_2$ is a photo-cross-linkable group comprising at least one of a methacrylate group, an acrylate group, an alkenyl group, an epoxy group, or an acryloxy group, or $R_2$ is a group formed by photo-crosslinking said photo-cross-linkable group;
m is selected to be an integer in the range of 0 to about 10; and
n is selected to be an integer in the range of 2 to about 10.

13. The polymer of claim 12, wherein m is 0.
14. The polymer of claim 12, wherein n is an integer in the range of 3 to 7.
15. The polymer of any of claim 12, wherein n and $R_2$ in formula (IV) are selected such that $-(CH_2)_n-R_2$ is a propylmethacrylate group, a propylacrylate group, or an epoxypropyl group.
16. The polymer of claim 12, wherein the refractive index of the polymer is greater than 1.50 when measured at 633 nm.

17. The polymer of claim 12, wherein the refractive index of the polymer is greater than 1.50 when measured at 1550 nm.

18. The polymer of claim 12, wherein $R_2$ is a group formed by photo-crosslinking said photo-cross-linkable group.

19. The polymer of claim 18, wherein said photo-crosslinking is by exposure to UV light.

20. A sol-gel composition comprising a compound of the formula (V):

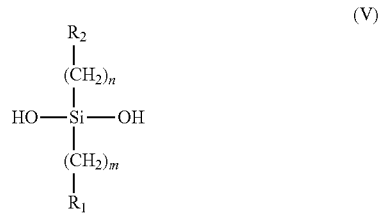

(V)

wherein $R_1$ is an optionally substituted aromatic group, wherein the aromatic group is selected from the group consisting of phenyl, biphenyl, naphthyl, anthracenyl, phenanthrenyl, quinolinyl, tetracenyl, pentacenyl, pyrenyl, and perylenyl; $R_2$ is a photo-cross-linkable group comprising at least one of a methacrylate group, an acrylate group, an alkenyl group, a vinyl group, an epoxy group, or an acryloxy group; m is selected to be an integer in the range of 0 to about 10; and n is selected to be an integer in the range of 2 to about 10; and a solvent, wherein the solvent is present in an amount of at least about 10% by weight based on the weight of the composition.

21. The sol-gel composition of claim 20, wherein the solvent is present in an amount of at least 20% by weight.

22. The sol-gel composition of claim 20, wherein the solvent comprises tetrahydrofuran.

23. The sol-gel composition of claim 20, wherein m is 0.

24. The sol-gel composition of claim 20, wherein n is an integer in the range of 3 to 7.

25. The sol-gel composition of claim 20, wherein n and $R_2$ in formula (I) are selected such that the $-(CH_2)_n-R_2$ portion of formula (V) is a propylmethacrylate group, a propylacrylate group, or an epoxypropyl group.

26. An optical device comprising:
a layer comprising a polymer that includes a recurring unit of the formula (VI):

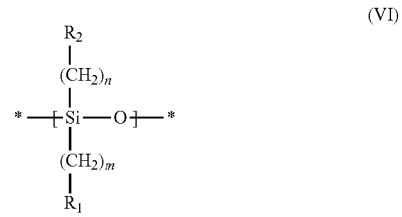

(VI)

wherein $R_1$ is an optionally substituted aromatic group, wherein the aromatic group is selected from the group consisting of phenyl, biphenyl, naphthyl, anthracenyl, phenanthrenyl, quinolinyl, tetracenyl, pentacenyl, pyrenyl, and perylenyl;

$R_2$ is a photo-cross-linkable group comprising at least one of a methacrylate group, an acrylate group, an alkenyl group, an epoxy group, or an acryloxy group;

m is selected to be an integer in the range of 0 to about 10; and n is selected to be an integer in the range of 2 to about 10.

27. The optical device of claim 26 in the form of a waveguide.

* * * * *